(12) United States Patent
Burbank et al.

(10) Patent No.: US 6,635,065 B2
(45) Date of Patent: *Oct. 21, 2003

(54) DOPPLER DIRECTED SUTURE LIGATION DEVICE AND METHOD

(75) Inventors: Fred Burbank, San Juan Capistrano, CA (US); Michael L. Jones, Capistrano Beach, CA (US); Jill Uyeno, Mission Viejo, CA (US); Greig E. Altieri, Laguna Beach, CA (US); R. J. Serra, Irvine, CA (US)

(73) Assignee: Vascular Control Systems, Inc., San Juan Capistrano, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/909,124

(22) Filed: Jul. 17, 2001

(65) Prior Publication Data

US 2002/0068951 A1 Jun. 6, 2002

Related U.S. Application Data

(63) Continuation-in-part of application No. 09/713,020, filed on Nov. 16, 2000.

(51) Int. Cl.⁷ ............................................... A61B 17/00
(52) U.S. Cl. ...................... 606/148; 606/139; 606/144; 600/453
(58) Field of Search ................................. 606/139, 144, 606/142, 145, 157; 600/437, 439, 462, 411, 453, 463; 128/898

(56) References Cited

U.S. PATENT DOCUMENTS 3,209,753 A   10/1965   Hawkins et al.
3,411,505 A   11/1968   Nobis (List continued on next page.)

FOREIGN PATENT DOCUMENTS

DE   195 28 440 A   2/1997
DE   200 22 012 U1  5/2001

(List continued on next page.)

OTHER PUBLICATIONS

Barth, Klemens H. et al., "Long Term Follow–Up of Transcatheter Embolization With Autologous Clot, Oxycel and Gelfoam in Domestic Swine", *Investigative Radiology*, May–Jun. 1977, vol. 12, pp. 273–290.

(List continued on next page.)

*Primary Examiner*—Michael J. Milano
*Assistant Examiner*—Julian W. Woo
(74) *Attorney, Agent, or Firm*—Duane Morris LLP

(57) ABSTRACT

Exemplary embodiments are directed to providing a method of preparing an anatomical vessel contained within a tissue bundle for ligation, including positioning a cannula adjacent to the tissue bundle, wherein the positioning is non-penetrating, the cannula including a first extendable member, a second extendable member, a Doppler wand, and a distal end, transmitting ultrasound signals toward the vessel through the tissue bundle with the Doppler wand, receiving ultrasound signals reflected by the vessel through the tissue bundle with the Doppler wand, invaginating the tissue bundle with the first extendable member on a first side of the tissue bundle, invaginating the tissue bundle with the second extendable member on a second side of the bundle opposite the first side, and interpenetrating a length of ligation material between the first and second extendable members on a side of the vessel opposite the cannula distal end.

13 Claims, 17 Drawing Sheets

U.S. PATENT DOCUMENTS

| | | |
|---|---|---|
| 4,292,960 A | 10/1981 | Paglione |
| 4,428,379 A | 1/1984 | Robbins et al. |
| 4,509,528 A | 4/1985 | Sahota |
| 4,650,466 A | 3/1987 | Luther |
| 4,757,823 A | 7/1988 | Hofmeister et al. |
| 4,991,588 A | 2/1991 | Pflueger et al. |
| 4,994,069 A | 2/1991 | Ritchart et al. |
| 5,037,433 A | 8/1991 | Wilk et al. |
| 5,081,997 A | 1/1992 | Bosley, Jr. et al. |
| 5,108,408 A | 4/1992 | Lally |
| 5,201,314 A | 4/1993 | Bosley et al. |
| 5,226,911 A | 7/1993 | Chee et al. |
| 5,275,166 A | 1/1994 | Vaitenkunas et al. |
| 5,289,831 A | 3/1994 | Bosley |
| 5,336,229 A | 8/1994 | Noda |
| 5,336,231 A | 8/1994 | Adair .................... 606/148 |
| 5,383,922 A | 1/1995 | Zipes et al. |
| 5,456,693 A | 10/1995 | Conston et al. |
| 5,458,596 A | 10/1995 | Lax et al. |
| 5,488,958 A | 2/1996 | Topel et al. |
| 5,496,331 A | 3/1996 | Xu et al. |
| 5,507,744 A | 4/1996 | Tay et al. |
| 5,542,944 A | 8/1996 | Bhatta |
| 5,549,624 A | 8/1996 | Mirigian et al. |
| 5,549,824 A | 8/1996 | Trumpf et al. |
| 5,556,396 A | 9/1996 | Cohen et al. |
| 5,570,692 A * | 11/1996 | Morinaga .................. 600/453 |
| 5,588,960 A | 12/1996 | Edwards et al. |
| 5,614,204 A | 3/1997 | Cochrum |
| 5,658,299 A | 8/1997 | Hart |
| 5,662,676 A | 9/1997 | Koninckx |
| 5,662,680 A | 9/1997 | Desai |
| 5,665,096 A | 9/1997 | Yoon |
| 5,672,153 A | 9/1997 | Lax et al. |
| 5,672,172 A | 9/1997 | Zupkas |
| 5,691,314 A | 11/1997 | Hodgen |
| 5,697,942 A | 12/1997 | Palti |
| 5,702,407 A | 12/1997 | Kaji |
| 5,713,896 A | 2/1998 | Nardelia |
| 5,713,942 A | 2/1998 | Stern et al. |
| 5,715,832 A | 2/1998 | Koblish et al. |
| 5,716,389 A | 2/1998 | Walinsky et al. |
| 5,720,743 A | 2/1998 | Bischof et al. |
| 5,759,154 A | 6/1998 | Hoyns |
| 5,766,135 A | 6/1998 | Terwilliger |
| 5,776,129 A | 7/1998 | Mersch |
| 5,797,397 A | 8/1998 | Rosenberg |
| 5,800,378 A | 9/1998 | Edwards et al. |
| 5,817,022 A | 10/1998 | Vesely |
| 5,836,906 A | 11/1998 | Edwards |
| 5,840,033 A | 11/1998 | Takeuchi |
| 5,895,386 A | 4/1999 | Odell et al. |
| 5,899,861 A | 5/1999 | Friemel et al. |
| 5,910,484 A | 6/1999 | Haupert, Jr. |
| 5,911,691 A | 6/1999 | Mochizuki et al. |
| 5,921,933 A | 7/1999 | Sarkis et al. |
| 5,941,889 A | 8/1999 | Cermak |
| 5,979,453 A | 11/1999 | Savage et al. |
| 6,015,541 A | 1/2000 | Greff et al. |
| 6,019,724 A | 2/2000 | Gronningsaeter et al. ... 600/439 |
| 6,032,673 A | 3/2000 | Savage et al. |
| 6,033,398 A | 3/2000 | Farley et al. |
| 6,034,477 A | 3/2000 | Peeters et al. |
| 6,035,238 A | 3/2000 | Ingle et al. |
| 6,045,508 A | 4/2000 | Hossack et al. |
| 6,066,139 A | 5/2000 | Ryan et al. |
| 6,077,257 A | 6/2000 | Edwards et al. |
| 6,106,473 A | 8/2000 | Violante et al. |
| 6,231,515 B1 | 5/2001 | Moore et al. |
| 6,254,601 B1 | 7/2001 | Burbank et al. |
| 6,280,441 B1 | 8/2001 | Ryan |

FOREIGN PATENT DOCUMENTS

| | | |
|---|---|---|
| EP | 0 472 368 | 2/1992 |
| EP | 0 598 579 | 5/1994 |
| EP | 1 072 282 | 1/2001 |
| GB | 2 311 468 A | 1/1997 |
| WO | WO 95/02370 | 1/1995 |
| WO | WO 95/02371 | 1/1995 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 02/39904 A1 | 5/2002 |

OTHER PUBLICATIONS

Bateman, William M.D., "Treatment of intractable menorrhagia by bilateral uterine vessel, Interruption", *Am. J. Obst. & Gynec.* 89(6):825–827 (Jul. 15, 1964).

Brigato, G. et al., "A Noninvasive Instrumental Method in Severe Postpartum Hemorrhages", *Minerva Ginecologica* 50(7–8):337–339 (1998).

Brohim, Robert M. et al., "Development of Independent Vessel Security After Ligation With Absorbable Sutures or Clips", *The American Journal of Surgery*, Mar. 1993, vol. 165, pp. 345–348.

Burbank, Fred et al., "Uterine Artery Occlusion by Embolization or Surgery for the Treatment of Fibroids: A Unifying Hypothesis—Transient Uterine Ischemia", *The Journal of the American Association of Gynecologic Laparoscopists*, Nov. 2000, vol. 7, No. 7 Supplemental, pp. S3–S49.

Fuchs, Karl, "Afibrinogenemia Treated by Ligation of Uterine Arteries", *Gynacologic* 148:407–411 (1959).

Garza Leal, J. et al., "Myoma Treatment by Transient Uterine Ischemia", *The Journal of the American Association of Gynecologic Laparoscopists* 7(3):S31 (Aug. 2000).

Hay, D.L. et al., "Hemostasis in Blood Vessels After Ligation", *Am. J. Obstet. Gynecol.*, Mar. 1989, 160:3, pp. 737–739.

Hunerbein, M. et al., "Endoscopic Ultrasound–Guided Real Time Biopsy of Peri–Intestinal Tumors", *Surgical Technology International VII*, 1998, pp. 91–95.

O'Leary, James A., M.D., "Uterine Artery Ligation in the Control of Postcesarean Hemorrhage", *The Journal of Reproductive Medicine, Inc.*, 40(3):189–193 (Mar. 1995).

O'Leary, James L., M.D. et al., "Uterine artery ligation in the control of intractable postpartum hemorrhage", Am. J. Obst. & Gynec. 94(7):920–924 (Apr. 1, 1966).

Ravina, J.H. et al., "Arterial Embolisation to Treat Uterine Myomata", *The Lancet*, Sep. 9, 1995, vol. 346, No. 8976, pp. 671–672.

Schaefer, C.J. et al., "Absorbable Ligating Clips", *Surg. Gynecol. Obstet.*, 1982, 154:513–516.

"Mick 200–TP Applicator Package", Mick Radio–Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostrate Gland", Bruel & Kjaer Medical Systems, Inc., advertisement.

International Search Report for PCT/US02/09775 mailed Sep. 12, 2002.

International Search Report for PCT/US02/23347 mailed Nov. 20, 2002.

International Search Report for EP 99 96 7154 (PCT/US99/28101) mailed Dec. 3, 2002.

International Search Report for PCT/US02/22015 mailed Dec. 3, 2002.

* cited by examiner

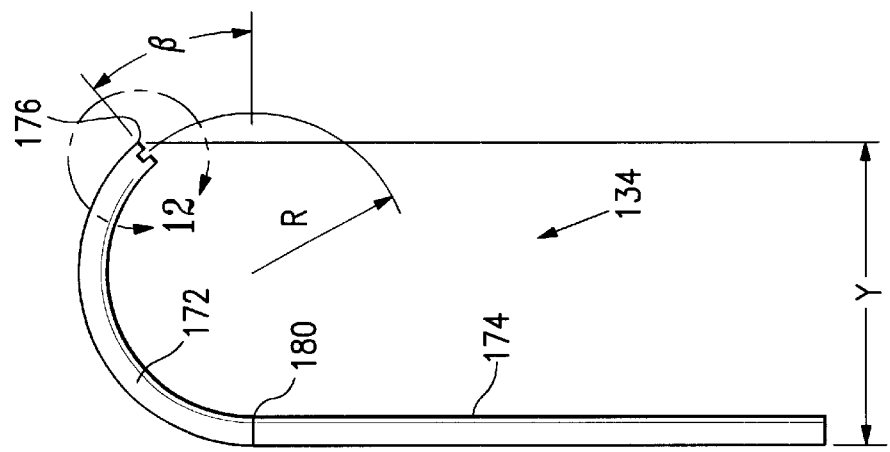
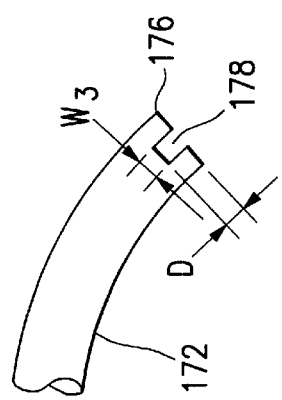
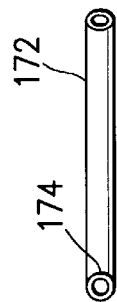
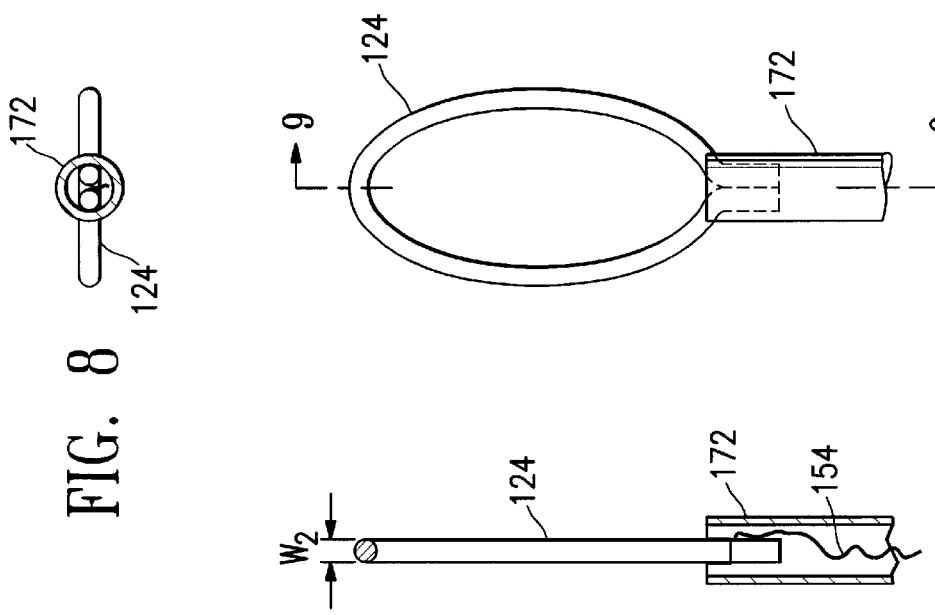

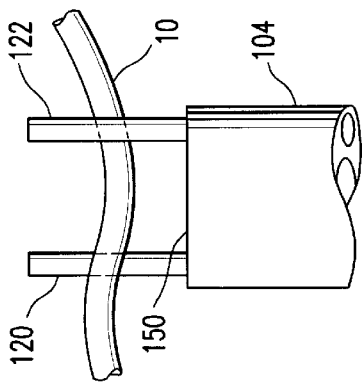
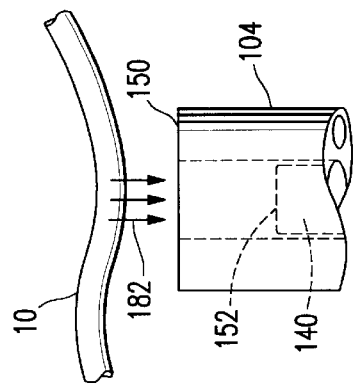
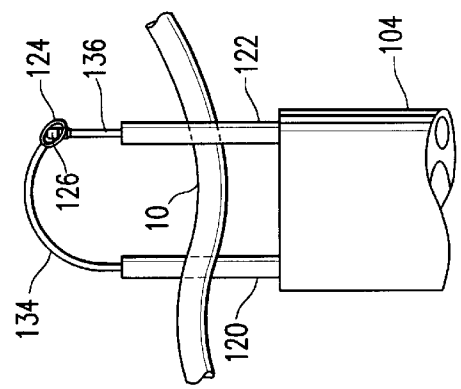
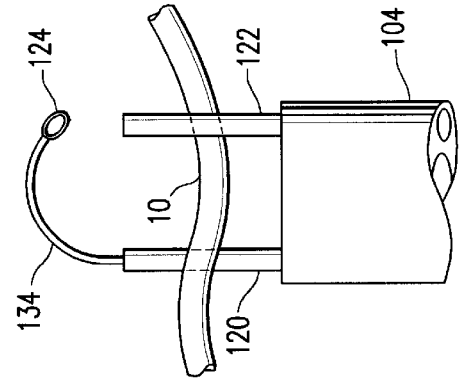
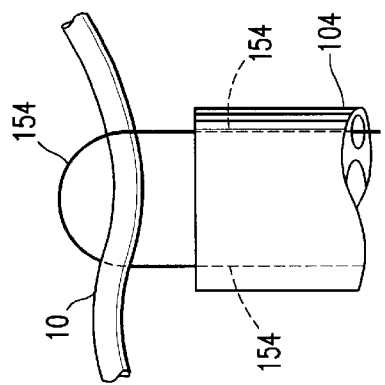

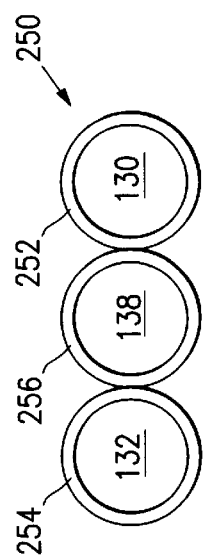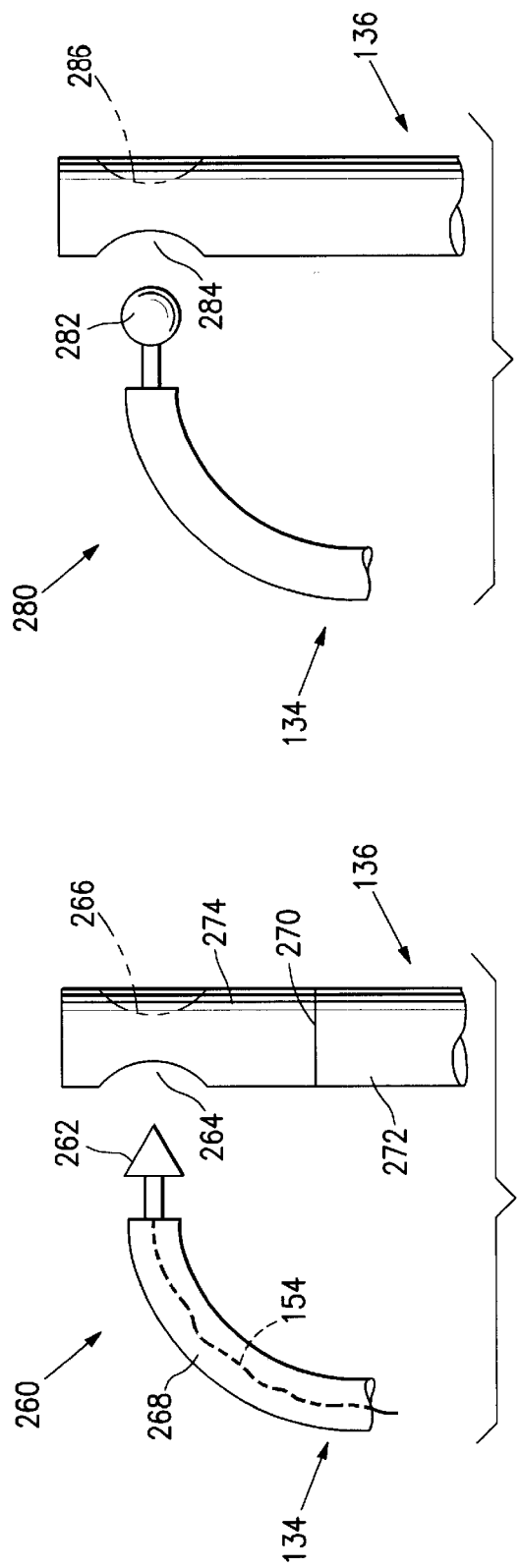

DOPPLER DIRECTED SUTURE LIGATION DEVICE AND METHOD

This is a Continuation-in-Part application of the Original application U.S. patent Ser. No. 09/713,020, filed on Nov. 16, 2000, entitled Doppler Directed Suture Ligation Device and Method by Fred Burbank, Michael L. Jones, Jill Uyeno, Greig E. Altieri, and R. J. Serra.

BACKGROUND OF THE INVENTION

1. Field of the Invention

The present invention relates to ligation devices and methods, and more particularly to devices and methods for accurately locating and ligating an anatomical vessel.

2. Brief Description of the Related Art

The Doppler effect is currently utilized in many fields. For example, Doppler stethoscopes and Doppler wands are currently utilized to listen to the blood flow within the anatomical structures in patients, especially in mammalian patients. Continuous wave Doppler sound signals are used to identify blood vessels, but do not provide feedback as to the distance of the vessel from the Doppler probe used. Pulsed wave Doppler has been used to identify blood vessels and, in conjunction with two dimensional (2D) imaging systems, identify the distance to a blood vessel and blood flow characteristics. Ultrasound systems with Doppler imaging are also currently used in medical fields, and typically produce gray-scale two-dimensional images. The addition of Doppler processing allows for the evaluation of fluid flow velocities through fluid conduits within the patient, and the relative position of these vessels to other anatomical structures.

Ligation devices have previously been proposed. These prior ligation devices have typically been used in laparascopic procedures, and have typically required that the anatomical feature of interest be dissected or visualized prior to ligation of that feature. Other ligation devices require the penetration of a tissue bundle encapsulating the anatomical vessel in order to perform location and ligation of the vessel.

The tissue of the vaginal wall is very elastic, pliable, and flexible. The vaginal wall can made to assume different shapes without tearing and without significant patient discomfort or pain. Heretofore, this inherent characteristic of these tissues has not been utilized in the area of tissue ligation.

SUMMARY OF THE INVENTION

According to a first exemplary embodiment, a method of preparing an anatomical vessel contained within a tissue bundle for ligation, comprises the steps of positioning a cannula adjacent to the tissue bundle, wherein the positioning is non-penetrating, the cannula including a first extendable member, a second extendable member, a Doppler wand, and a distal end, transmitting ultrasound signals toward the vessel through the tissue bundle with the Doppler wand, receiving ultrasound signals reflected by the vessel through the tissue bundle with the Doppler wand, invaginating the tissue bundle with the first extendable member on a first side of the tissue bundle, invaginating the tissue bundle with the second extendable member on a second side of the bundle opposite the first side, and interpenetrating a length of ligation material between the first and second extendable members on a side of the vessel opposite the cannula distal end.

According to a second exemplary embodiment, a ligation device for invaginating a vessel contained within a tissue bundle comprises a means for noninvasively positioning a cannula about the tissue bundle, the cannula including a Doppler wand and a distal end, a means for transmitting ultrasound signals toward the vessel through the tissue bundle with the Doppler wand, a means for receiving ultrasound signals reflected by the vessel through the tissue bundle with the Doppler wand, a first means for invaginating the tissue bundle on a first side of the tissue bundle, a second means for invaginating the tissue bundle on a second side of the bundle opposite the first side, and a means for interpenetrating a length of ligation material between the first and second invaginating means on a side of the vessel opposite the cannula distal end.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIGS. 8–10 illustrate a loop in accordance with the present invention;

FIGS. 11–13 illustrate portions of the device illustrated in FIG. 1;

FIGS. 20–24 illustrate the device of FIG. 1 used in accordance with an exemplary embodiment of a method of ligating an anatomical feature in a patient;

FIG. 25 illustrates portions of yet another embodiment of the present invention;

FIGS. 26A and 26B illustrate portions of further embodiments of the present invention;

DESCRIPTION OF PREFERRED EMBODIMENTS

Figure 1:
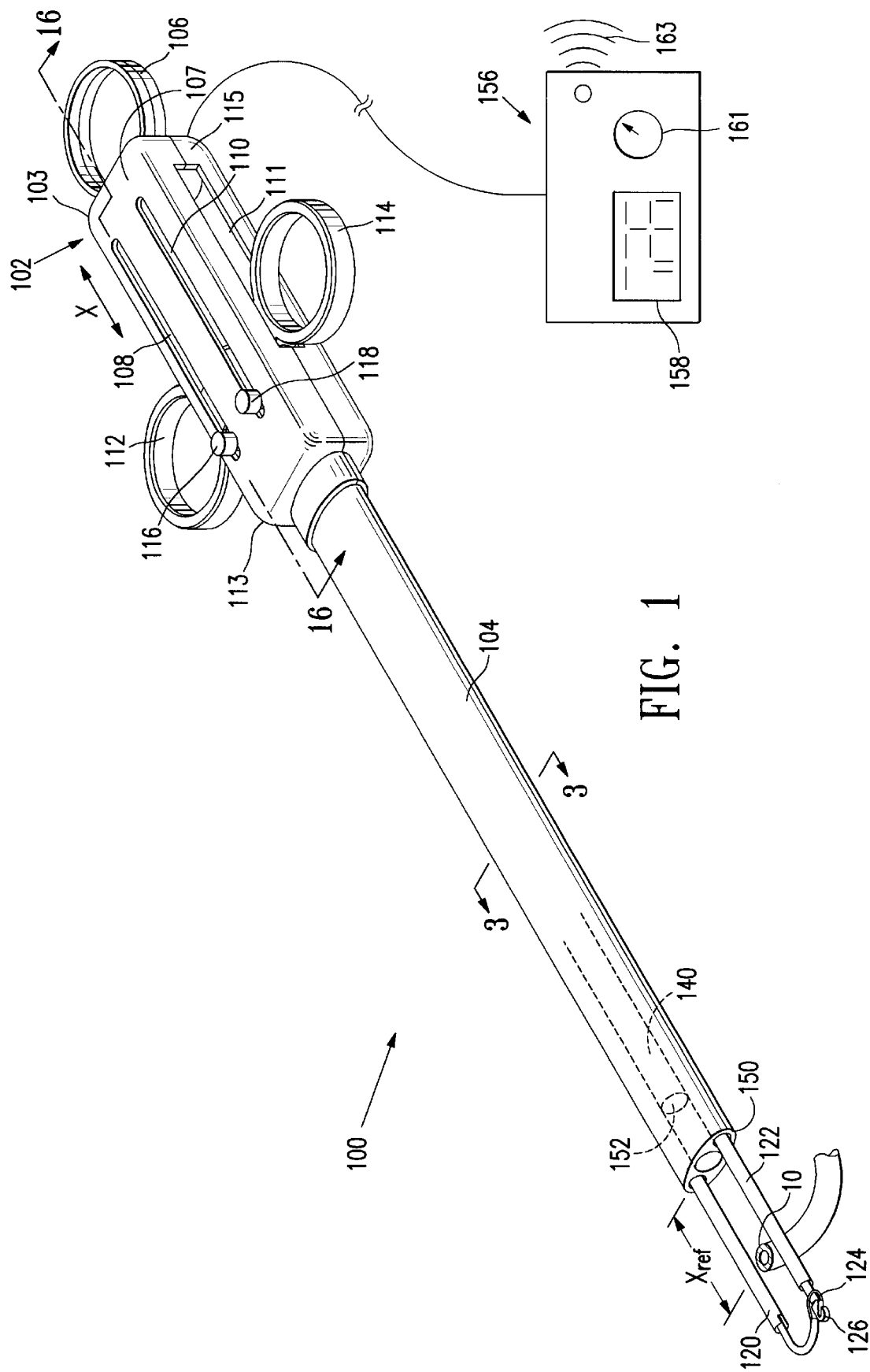
FIG. 1 illustrates a top, distal, side perspective view of an exemplary embodiment of a Doppler directed ligation device in accordance with the present invention.

Referring to the drawing figures, like reference numerals designate identical or corresponding elements throughout the several figures.

FIG. 1 illustrates a top, distal end, side perspective view of an exemplary embodiment of a Doppler directed ligation device 100 in accordance with the present invention. FIG. 1 illustrates device 100 deployed to enable a practitioner to ligate a fluid vessel 10. While vessel 10 is preferably a uterine artery, other vessels, such as other arteries, veins, fallopian tubes, urinary ducts such as the ureter, and other fluid vessels can be ligated with device 100 within the spirit and scope of the present invention, as will be readily appreciated by one of ordinary skill in the art. Different from ligation devices which have previously been proposed, as well as their uses, ligation devices and methods in accordance with the present invention do not require dissection of the vessel 10, and does not require actual visualization of the vessel, prior to ligation. The capability enabled by the present invention of invaginally advancing a ligation device either through or around tissue beds and/or tissue planes without the need for dissection or tissue penetration in order to locate vessel 10 can provide benefits as described elsewhere herein and as will be readily appreciated by one of ordinary skill in the art.

Figure 2:
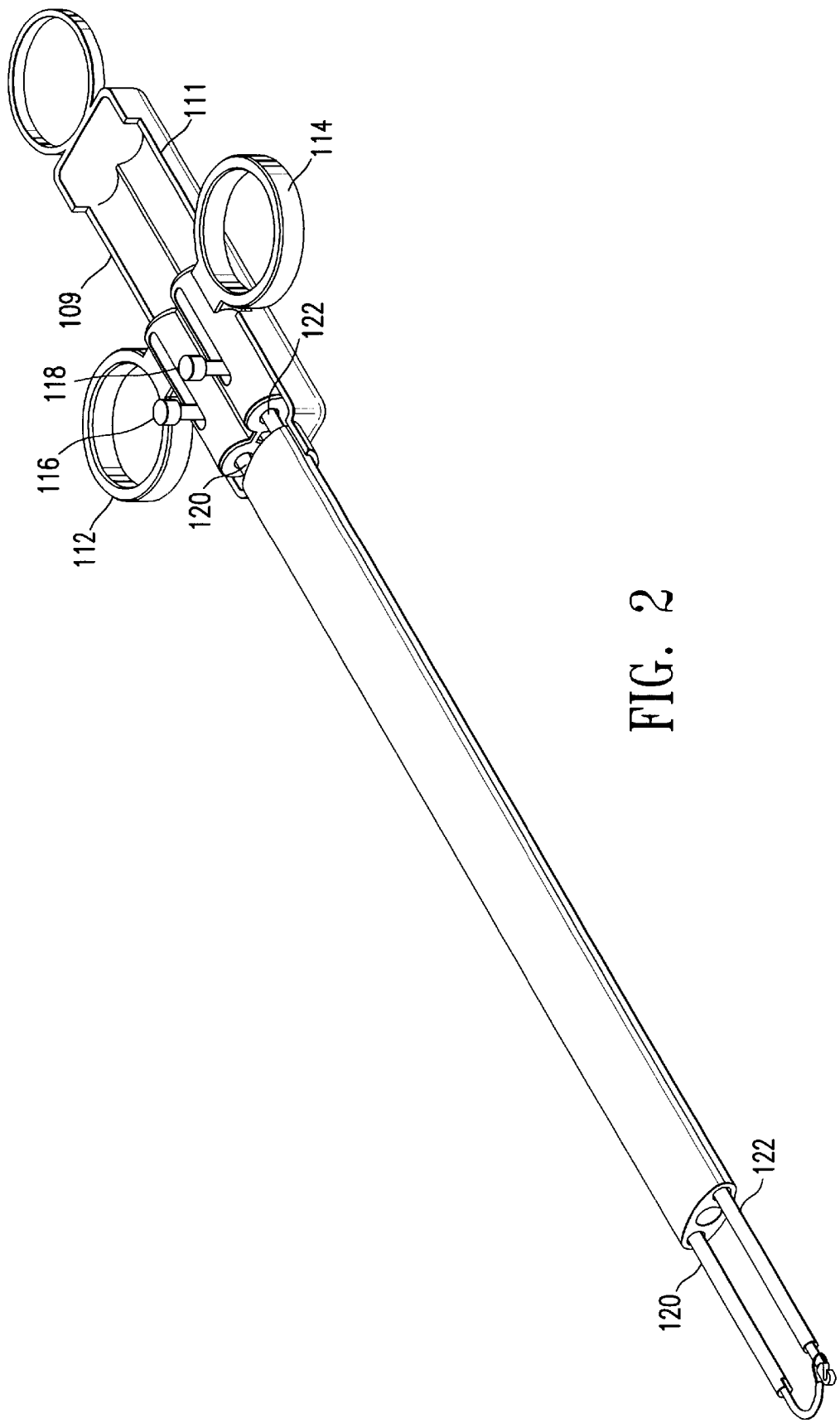
FIG. 2 illustrates the ligation device of FIG. 1, with portions removed.

Ligation device 100 includes a proximal handle 102 and a cannula 104 extending distally from the handle. Handle 102 includes a hollow housing 103 sized and shaped to fit comfortably in the hand of a practitioner. A proximal thumb ring 106 is fixed to the housing 103 opposite cannula 104. A pair of top slots 108, 110 are formed in the top surface 107 of the housing 103, and a pair of side slots 109, 111, are formed in the sidewalls 113, 115. A first actuation ring 112 and a second actuation ring 114 are slidably mounted in housing 103, through the opposite side slots 109, 111 (see also FIG. 2) of the housing. Upstanding tabs 116, 118, extend from the interior of housing 103, through slots 108, 110, respectively, to outside the housing. The slots 109,111 limit the range of motion of the rings 112, 114, and the slots 108, 110 function to limit the range of motion of the tabs 116, 118 along longitudinal direction X.

Figure 3:
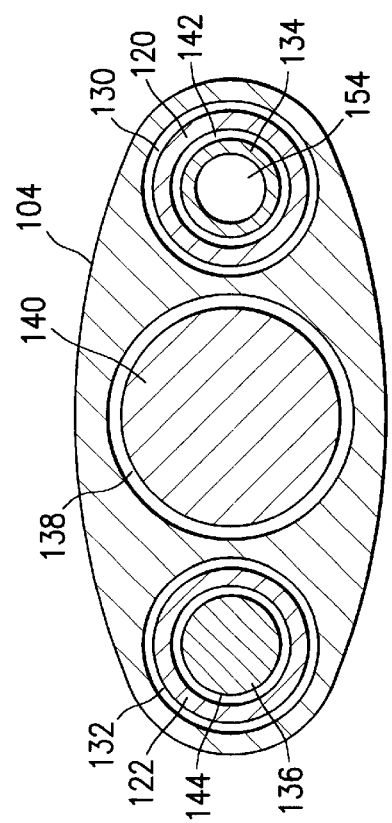
FIG. 3 illustrates a cross sectional view taken along line 3—3 in FIG. 1.

Cannula 104 is fixedly mounted to the distal end of handle 102. Cannula 104 includes a plurality of lumenae extending longitudinally through the cannula, which are best illustrated in FIG. 3. Ligation device 100 includes a first extendable element 120 which is longitudinally slidable through cannula 104 between a retracted position (see, e.g., FIG. 20) in which the first extendable element is housed entirely inside the cannula, and an extended position (see, e.g., FIG. 21) in which the first extendable element extends distally beyond the distal end 150 of the cannula. Ligation device also includes a second extendable element 122 which, similar to first extendable element 120, is longitudinally slidable through cannula 104 between retracted and extended positions. First and second extendable elements 120, 122 are connected to first and second actuation rings 112, 114, respectively, at the proximal ends of the extendable elements, so that the rings can be used to longitudinally advance and retract the extendable elements in cannula 104.

The first and second extendable elements 120, 122 are positioned laterally opposite each other in cannula 104, as best illustrated in FIG. 3, so that when they are in their extended positions they can be positioned on opposite sides of an anatomical vessel, such as vessel 10. Furthermore, first and second extendable elements 120, 122 are sized so that they both are extendable farther than a distance $X_{ref}$ from the distal end 150, described in greater detail below, so that a vessel 10 can be bracketed by the extendable elements when the vessel is within $X_{ref}$ from the distal end of cannula 104.

First extendable element 120 carries a detachable element at its distal end. In the embodiment illustrated in FIG. 1, the detachable element is a loop 124. Loop 124 is attached, either directly or indirectly as will be described in greater detail below, to a length of threadlike material, such as suture material, which may optionally further include a leader, which extends proximally through cannula 104. Second extendable element 122 carries a snare element which is sized and configured to grab, ensnare, or otherwise become secured with the detachable element of the first extendable element 120 when the first and second extendable elements are in their extended positions (see FIGS. 1 and 23). In the embodiment illustrated in FIG. 3, the snare element is a hook 126. Loop 124 and snare 126 will be described in greater detail below with reference to FIGS. 4–13.

Ligation device 100 further includes a Doppler ultrasound device or wand 140 mounted in the ligation device. In accordance with the present invention, the Doppler ultrasound device can be removably mounted in the ligation device, or the components of a Doppler ultrasound device can be integrated into the ligation device, e.g. into cannula 104, so as not to be removable. Thus, when the Doppler ultrasound device is removably mounted in ligation device 100, the Doppler ultrasound device can be removed at the termination of a use, removed from the remainder of the ligation device, and the Doppler ultrasound device sterilized and reused. Alternatively, when the Doppler ultrasound device's components are integrated into the ligation device 100, the entire ligation device can be disposed of at the conclusion of a use.

Cannula 104 includes a third center lumen 138 (see FIGS. 3 and 7) into which a removable Doppler wand 140 is removably inserted. According to certain embodiments of the present invention, a distal end 152 of the Doppler wand is proximal of the distal end 150 of the cannula. According to other embodiments of the present invention, the distal end 152 of the Doppler wand 140 is positioned at the distal end 150 of the cannula. According to other embodiments of the present invention, the distal end 152 of the Doppler wand 140 is positioned distal of the distal end 150 of the cannula. Preferably, housing 103 includes portions which receive the proximal portions of Doppler wand 140, so that the Doppler wand can be removed and reused after ligation device 100 has been used. For example and not by way of limitation, housing 103 can include portions which are hinged together and secured with a snap, lock, or the like, so that the housing can be opened up, a Doppler wand 140 inserted into ligation device 100, and the housing portions closed and locked to secure the Doppler wand in the ligation device.

Doppler ultrasound wands suitable for use in the present invention are presently commercially available. For example, Koven model ES 100X MiniDop VRP-8 probe (St. Louis, Mo.) is a Doppler wand suitable for use as Doppler wand 140, and DWL/Neuro Scan Medical Systems' Multi-Dop B+ system with their 8 MHz handheld probe (Sterling, Va.) is a continuous and pulsed wave Doppler wand suitable for use as wand 140. Commercially available Doppler stethoscopes or wands have an ultrasound dispersion pattern which is generally conical, i.e., the wand "looks" out along a cone-shaped portion of a plane originating at the end of the wand. Thus, vessels with fluid flow in them, such as a blood vessel, which lie anywhere in this conical plane and within the effective range of the wand would be picked up by the wand. Doppler wands presently available are attached to a signal processing and display unit 156, which processes the electrical signals generated by wand 140 to generate displays and/or other data derived from the electrical signals for additional uses. Alternatively, the Doppler system can be gated to identify blood vessels within a predetermined distance range, e.g. from between 0 to 5 cm, more preferably between 0.5 and 3 cm.

Unit 156 includes a display 158 which indicates the distance from the distal tip 152 the source of reflected ultrasound waves is located, e.g., vessel 10. This information is typically calculated utilizing a predetermined function, because the distance is a function of the time it takes for the ultrasound waves to travel to and from the wand. Unit 156 preferably also includes a display or meter 160 of the magnitude of the reflected ultrasound waves's Doppler shift, which is the indication of the velocity of the fluid flowing through vessel 10. Unit 156 also preferably includes a sound source 162 which gives an audible indication of the Doppler shift, which can be louder when the Doppler shift is greater or the vessel is optimally positioned.

In the ligation device of the present invention, however, such a wide conical "field of view" typically returned by many commercially available Doppler wands is not preferable, because the practitioner is concerned with locating the vessel between the extendable elements in order to ligate the vessel. Were the present invention to utilize such "wide-view" Doppler wands without narrowing or otherwise affecting their field of view, vessels which are not directly distal of ligation device 100 would be picked up by the device, and would return Doppler shift data for vessels not of interest in the use of the ligation device. Ligation device 100, and specifically cannula 104, is therefore sized so that the distalmost end 152 of Doppler wand 140 is spaced proximally from the distal end 150 of the cannula, for use with "wide-view" wands to collimate the signal. Some commercially available Doppler wands, such as the aforementioned DWL probe, however, produce a sufficiently collimated signal so that further collimation is not necessary.

When utilizing a Doppler probe which does not produce a sufficiently collimated signal, lumen 138 is preferably coated, formed of a material, or is otherwise provided with a sleeve of a material on the interior surface of which collimates the sound waves emanating from Doppler wand 140. By way of example and not of limitation, lumen 138 can be coated or formed of polycarbonate, although other materials are also usable within the spirit and scope of the present invention.

The result of spacing distal end 152 proximally of distal end 150, and optionally further providing a material and/or sleeve which acoustically collimates the ultrasound waves from wand 140, is that ligation device 100 is substantially unidirectional in its Doppler field of view in a direction parallel with, and preferably between, first and second extendable elements 120, 122, and longitudinally distal of distal end 150. Stated differently, ligation device 100 is capable of receiving reflected ultrasound waves, originating from Doppler wand 140, reflected back from anatomical features directly distal of distal end 150. Thus, because distal end 152 is a fixed and known distance from distal end 150, and $X_{ref}$ is known, a maximum distance $X_{max}$ is predetermined by the structures of ligation device 100 within which a vessel 10 must be in order for the ligation device to be capable of ligating it. Stated somewhat differently, once it is determined that a vessel is within a predetermined distance of distal end 152, which is indicated by the time lag of the reflected ultrasound waves, ligation device 100 can be used to ligate that vessel.

According to another embodiment in accordance with the present invention, a Doppler wand can be chosen which has a "field of view" which is narrow enough that, when used in the combination of the ligating device 100, additional collimation structures are not necessary. For example, selection of a probe is based on its field of view and its operating frequency, and should also be based on the distance between the target artery and the Doppler probe so that the probe's depth of view is larger than this distance yet not so long as to include other blood vessels. By way of example and not of limitation, a Koven Doppler probe as described above can be used as wand 140 without requiring either a collimating sleeve and without spacing the distal end proximal of distal end 150. In general, Doppler wands suitable for use as Doppler wand 140 are selected with small enough diameter to be insertable in cannula 104, preferably operate at a frequency which is sufficiently sensitive to blood flow to monitor uterine artery blood flow, have a relatively narrow field of view and limited depth of view so as not to generate a signal from other blood vessels, and can be based on either pulsed or continuous wave Doppler signals.

Figure 7:
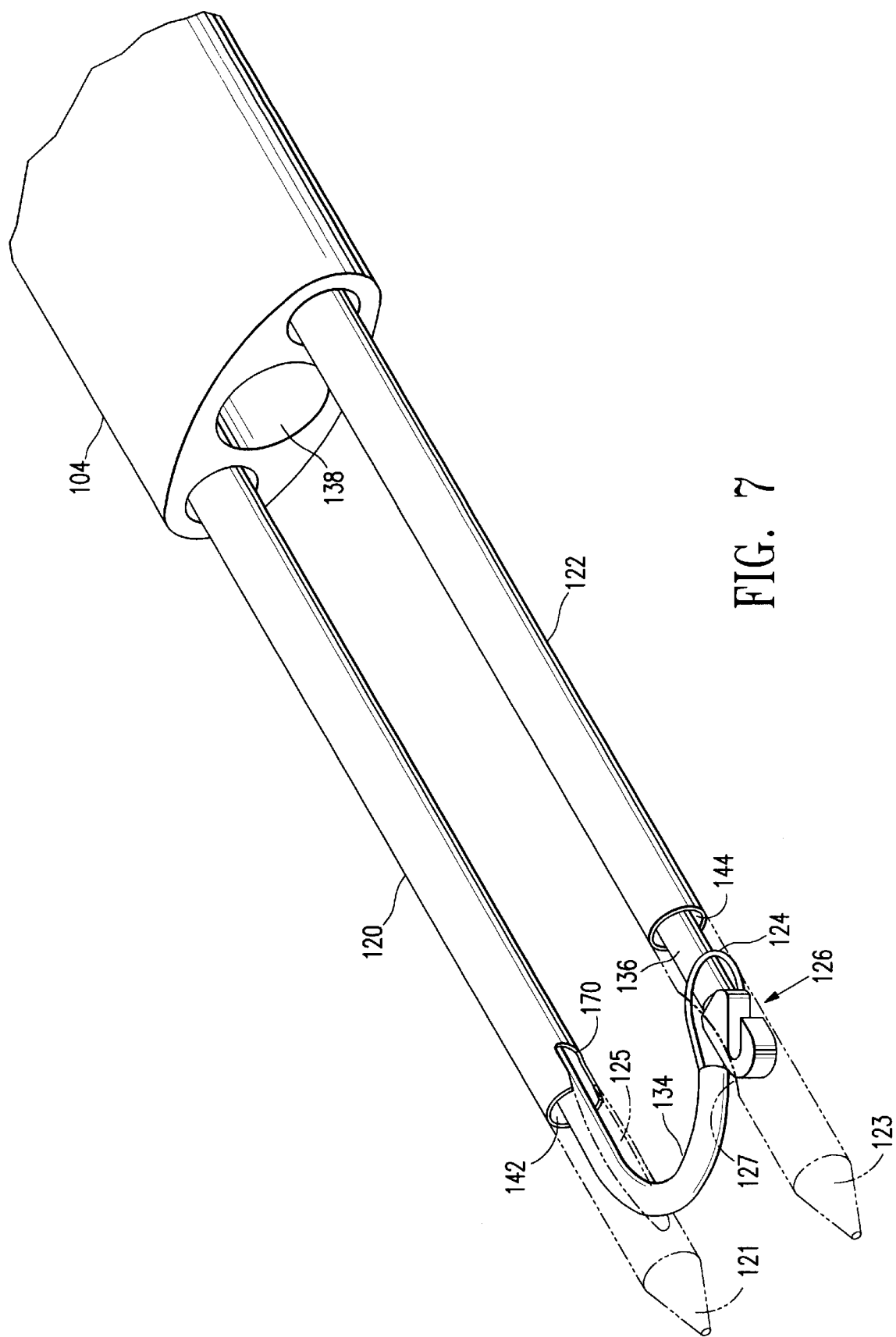
FIG. 7 illustrates an enlarged perspective view of the distal end of the embodiment illustrated in FIG. 1.

FIG. 3 illustrates a cross-section view of ligation device 100, as seen along line 3—3 in FIG. 1, and FIG. 7 illustrates an enlarged distal end perspective view of ligation device 100. Cannula 104 preferably has an oval cross sectional profile, so that the cannula can be relatively compact while still meeting the requirement that Doppler wand 140 be laterally between extendable elements 120, 122. As illustrated in FIG. 3, cannula 104 includes a first lumen 130 which longitudinally and slidingly receives first extendable element 120. Preferably, element 120 itself includes a lumen 142 through which a tubular suture and loop advancing element 134 is longitudinally slidable. Element 120 further optionally is provided with a slot or cutout 170 at its distal end in the wall of the element 120 adjacent to or facing element 122, to assist in guiding or positioning loop advancing element 134 in a desired direction and to assist in preventing rotation of the loop advancing element relative to the element 120.

Suture advancing element 134 at least in part is formed of a superelastic material, less preferably a shape-memory alloy (SMA) material, also less preferably (surgical) stainless steel. NiTi (nitinol) is preferred, although other superelastic, SMA, and biocompatible materials are within the scope of the present invention. Forming at least portions of suture advancing element 134 of NiTi allows the suture advancing element to be preformed with a curved distal end, so that the suture advancing element can be easily retracted into first extendable element 120, yet the distal end will accurately position loop 124 to be snared by extendable element 122 when the suture advancing element is advanced out of the first extendable element.

Suture/loop advancing element 134 preferably is a hollow tube and includes structure at the distal end of the element which holds loop 124, the loop in turn being attached to a length of suture material 154 (see also FIG. 24). A more detailed description of the structures at the distal ends of extendable elements 120, 122 is presented below with reference to FIGS. 4–13.

Cannula 104 includes a second lumen 132 in which second extendable element 122 is longitudinally slidably received. Second extendable element 122 preferably includes a lumen 144 which longitudinally slidably receives an extendible hooking or snaring element 136. Cannula 104 also includes a third lumen 138 which removably receives Doppler wand 140, so that the Doppler wand can be used with the other structures of ligation device 100 and then disassembled, as discussed above. Optionally, the ligation device 100, including the third lumen 138, can non-removably house the functional components of a Doppler wand, so that the entire ligation device can be conveniently disposed of.

As illustrated in FIG. 7, the first and second extendable elements 120, 122 can optionally further be provided with closed, preferably conically or frustoconically shaped tips 121, 123, respectively. The closed tips 121, 123 permit the extendable elements 120, 122 to be more easily advanced through tissue beds and planes. As described herein concerning another embodiment of the present invention, the extendable elements 120, 122 may also invaginate the tissue beds and planes without penetration of the tissue, because of the inherent flexibility or pliability of the vaginal wall tissue. When provided with the closed tips 121, 123, the extendable elements 120, 122 further include laterally inwardly facing openings 125, 127 so that the elements 134, 136 can pass out of the elements 120, 122, as described elsewhere herein. Further optionally, the distal interiors of one or both of the closed tips can be provided with cam surfaces (not illustrated) to assist in guiding the detachable elements and/or the snaring elements.

Figure 6:
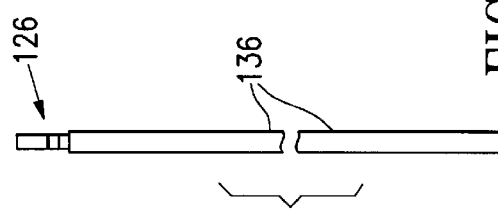
FIGS. 4–6 illustrate a snare in accordance with the present invention.
Figure 5:
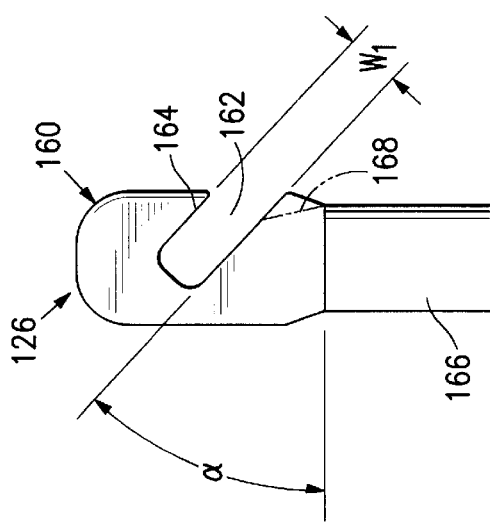
Figure 4:
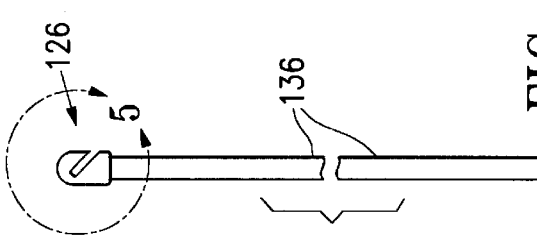

FIGS. 4–6 illustrate several views of snaring element 136 including hook or snare 126. As detailed in FIG. 5, snare 126 includes an enlarged head 160 having an angled slot 162. A hook portion 164 is formed distally of slot 162. Slot 162 has a width $W_1$ and extends into head 160 at an angle $\alpha$. A shank 166 is attached at the proximal end of head 160, and is preferably formed integrally therewith from a single piece of material. Alternatively, shank 166 and head 160 can be press-fit, welded, adhesively bonded, or otherwise formed separately and thereafter joined together as will be readily apparent to one of ordinary skill in the art. Width $W_1$ is selected to be greater than the width $W_2$ of loop 124 (see FIG. 9), so that the loop can be deflected into slot 162 by hook portion 164 and slide into the slot and be grabbed by snare 126. Optionally, the proximal portions of head 160 adjacent to the opening to slot 162 can be widened, as indicated in phantom lines in FIG. 5, which can facilitate loop 124 being deflected by hook portion 164 into slot 162.

FIGS. 8–13 illustrate distal end portions of suture/loop advancing element 134. As illustrated in FIGS. 8–10, loop 124 is preferably roughly oval in shape, and is temporarily mounted to the distal end of a tubular curved element 172 (see also FIG. 13). A length of suture material 154 or the like is tied, glued, crimped, or otherwise secured to loop 124, and extends proximally through tube 172. As illustrated in FIGS. 11–13, suture/loop advancing element 134 includes a straight portion 174 and a curved portion 172, both of which are hollow tubes. Straight portion 174 and curved portion 172 are joined together at a joint 180. Optionally, element 134 can be a monolithic element without such a joint 180, and a straight portion 174 and a curved portion 172 can be formed therein, as will be readily appreciated by one of ordinary skill in the art.

At least curved portion 172 of element 134 is preferably formed of a superelastic material. Alternatively, portion 172 can be formed of a SMA material. While the characteristics and use of superelastic materials are readily appreciated by one of ordinary skill in the art, a brief description as applied to curved portion 172 will aid in an understanding of the present invention. Portion 172 is preferably formed of a superelastic material, e.g., NiTi (nitinol). Portion 172 is given a curvature or bent configuration which, upon heating of the curved portion above a certain temperature for the superelastic material, is 'remembered' by the curved portion. In the embodiment illustrated in FIGS. 11–13 curved portion 172 is formed into an arc having a radius R and the distal end 176 being at an angle $\beta$ from a line perpendicular to straight portion 174. Distal end 176, when curved portion 172 is in its curved configuration, is a lateral distance Y from the straight portion 174.

The length of curved portion 172 and the shape, as well as the distance Y, are selected so that when curved portion 172 is in its curved configuration, loop 124 is positioned directed distally of second extendable element 122. In this location, snare 126 can be extended and can hook loop 124, to be pulled from suture/loop advancing element 134. The angular orientation of the lateral direction in which curved portion 172 extends when in its curved configuration can be preset so that loop 124 registers or lines up with snare 126, and slot 170 assists in maintaining this orientation. This present angular orientation can be determined, by way of example and not of limitation, by heating curved portion 172 above its transition temperature and rotating element 134 until loop 124 is directly distal of snare 126, prior to using device 100.

Curved portion 172 and straight portion 174 can both be formed of the same (superelastic) material. Alternatively, only portion 172 is formed of an superelastic material, and straight portion 174 can be formed of another material, e.g., stainless steel, and the two portions 172, 174 can be joined together at joint 180, as by welding, crimping, swaging, adhesive bonding, or the like. The distalmost end of portion 172 includes a slot 178 in which loop 124 is temporarily held. Slot 178 has a width $W_3$ and a depth D selected so that loop 124 can be received therein by a press fit, or loosely received and crimped therein. Loop 124 is not permanently held in slot 178, however, and is mounted in the slot so that the loop can be pulled out of the slot by a preselected force transmitted by snare 126 after the loop has been hooked by the snare (see, e.g., FIG. 3).

Figure 14:
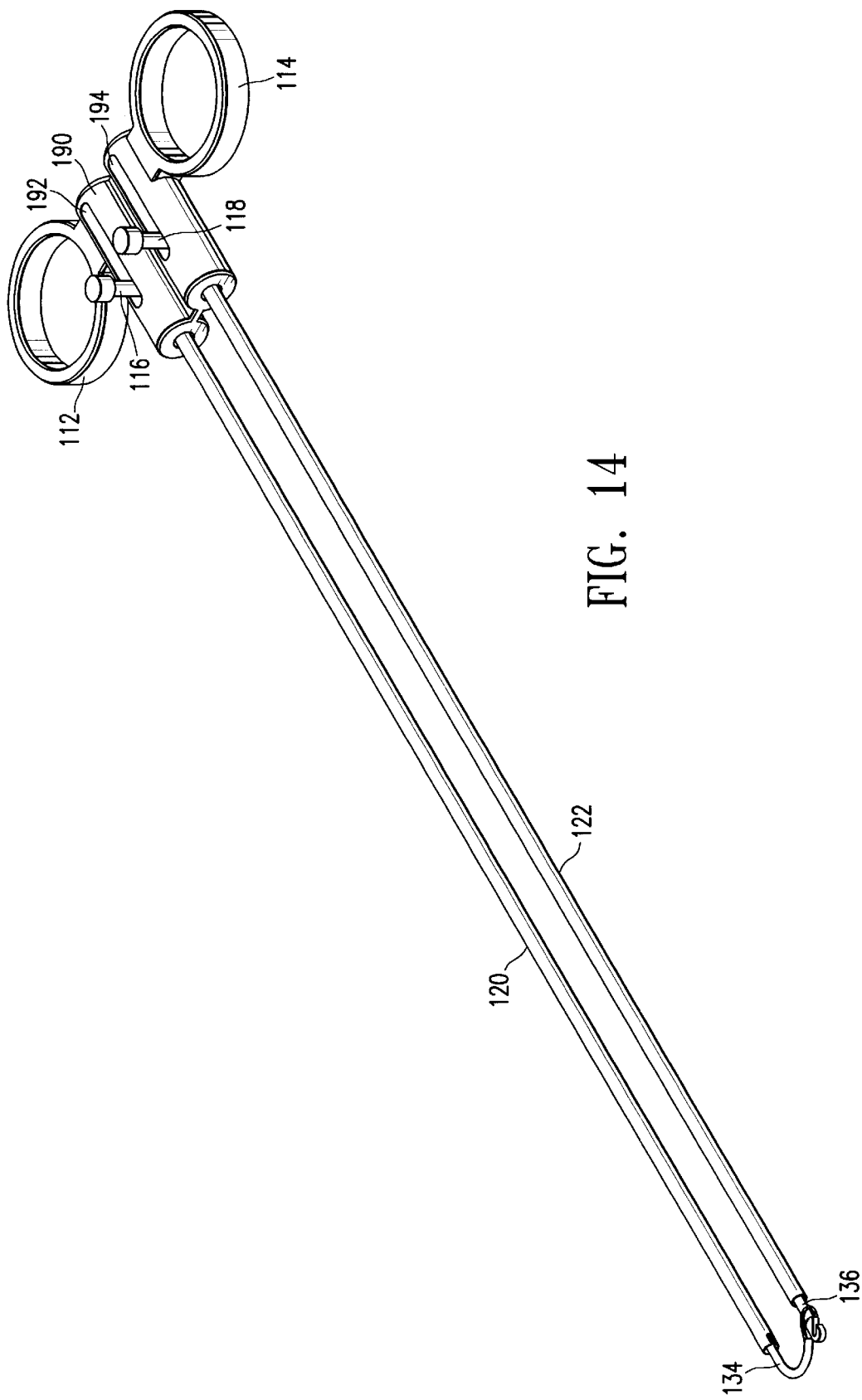
FIG. 14 illustrates a portion of the device illustrated in FIG. 1.

FIG. 14 illustrates internal portions of ligation device 100. First and second extendable elements 120, 122 are mounted in a block 190 to which rings 112, 114 are also fixedly secured. Thus, as described above, proximal and distal longitudinal movement of rings 112, 114 moves first and second extendable elements 120, 122. Block 190 includes a pair of slots 192, 194 formed in a top surface thereof in which tabs or pins 116, 118 are slidably received, respectively. Thus, the slots 192, 194 constrain the tabs 116, 118 laterally, while permitting them to move longitudinally over a range limited by the length of the slots.

Figure 15:
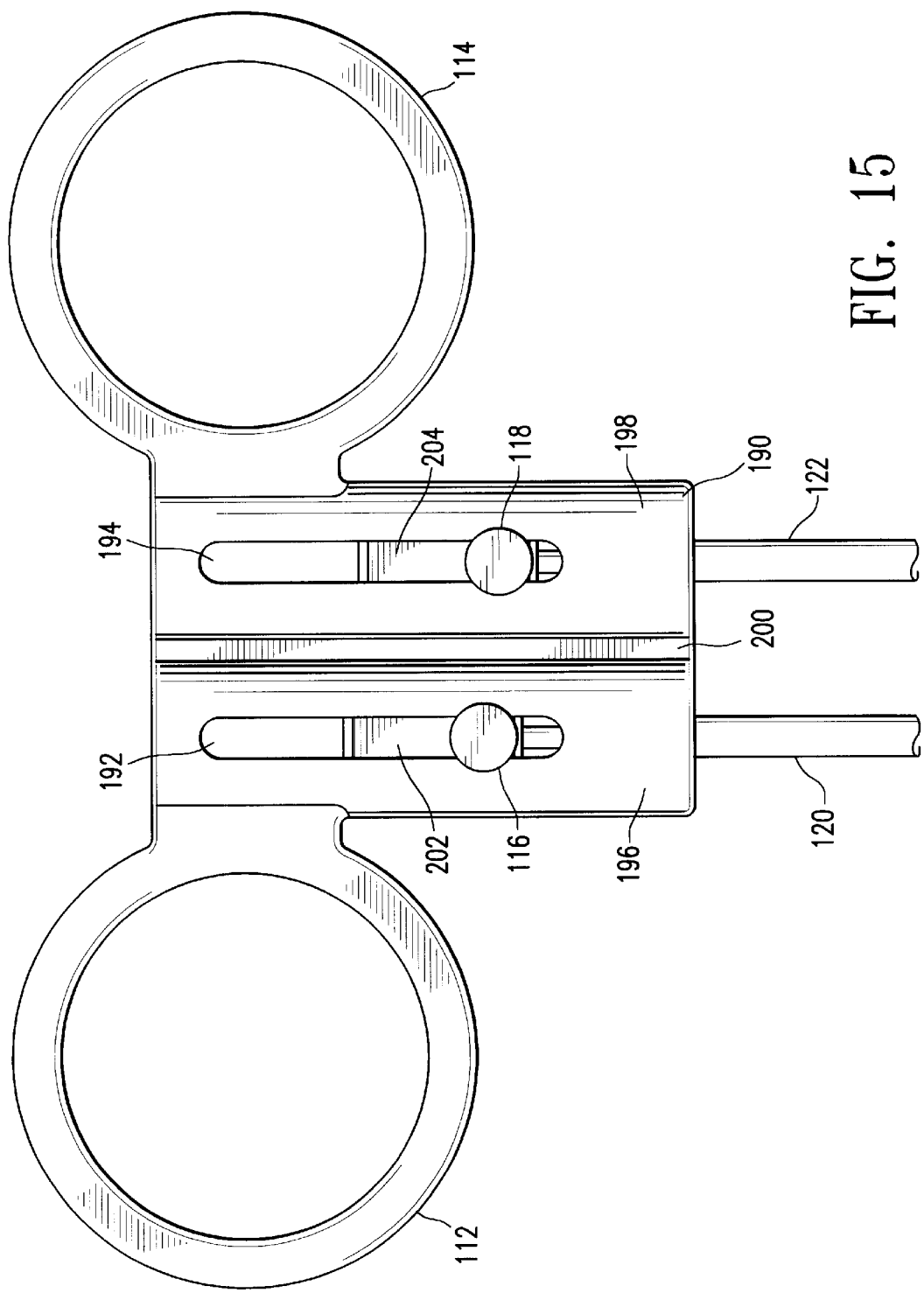
FIG. 15 illustrates an enlarged view of the portions illustrated in FIG. 14.

FIG. 15 illustrates a top plan view of distal portions of the view illustrated in FIG. 14. As can be seen in FIG. 15, the block 190 includes slots 192, 194, described above. According to one embodiment of the present invention, block 190 includes first and second lateral portions 196, 198, which are cylindrical in shape, in which the first and second extendable elements 120, 122 are mounted, respectively. According to one embodiment of the present invention, lateral portions 196, 198 can be fixedly joined together as a with a web 200, so that movement of one of the rings 112, 114 moves both lateral portions. According to yet another embodiment of the present invention, lateral portions 196 and 198 are not joined together, and are therefore separately and individually longitudinally moveable in housing 103.

Also visible in FIG. 15 are mounting blocks 202 and 204 positioned in block 190. Mounting block 202 fixedly receives the proximal portion of extendable element 134 and lower portions of tab 116, and mounting block 204 fixedly receives the proximal portion of extendable element 136 and tab 118. Block 202 thus joins together extendable element 134 with tab 116, and block 204 thus joins together extendable element 136 with tab 118. Additionally, blocks 202 and 204 constrain tabs 116 and 118 from being pulled up and out from block 190, as their lateral extents are larger than slots 192, 194, respectively.

Figure 16:
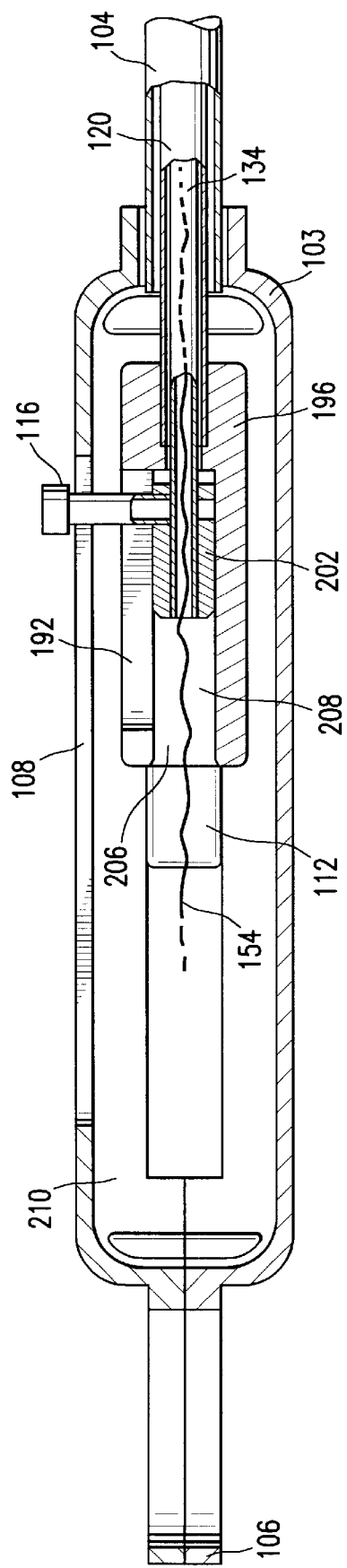
FIG. 16 illustrates a cross sectional view taken along line 16—16 in FIG. 1.

FIG. 16 illustrates a cross-sectional view of proximal portions of ligation device 100. As can be seen in FIG. 16, the housing 103 includes an interior chamber or cavity 210 which slidingly receives block 190 and its components. Block 190 includes an interior chamber or cavity 208 which slidingly receives blocks 202 and 204 (block 204 is not visible in the view of FIG. 16), and a proximal opening 206 which communicates interior chamber 208 with interior chamber 210. Proximal opening 206 also permits blocks 202, 204 to extend into interior chamber 210. FIG. 16 also illustrates suture 154 extending through loop advancing element 134, block 202, interior chamber 208, interior chamber 210, and exiting housing 103 through one of slots 108–111.

Figure 17:
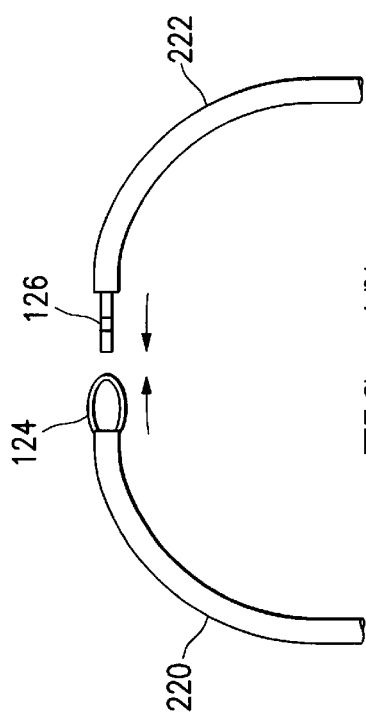
FIGS. 17–19 illustrate enlarged plan views of further embodiments in accordance with the present invention.
Figure 19:
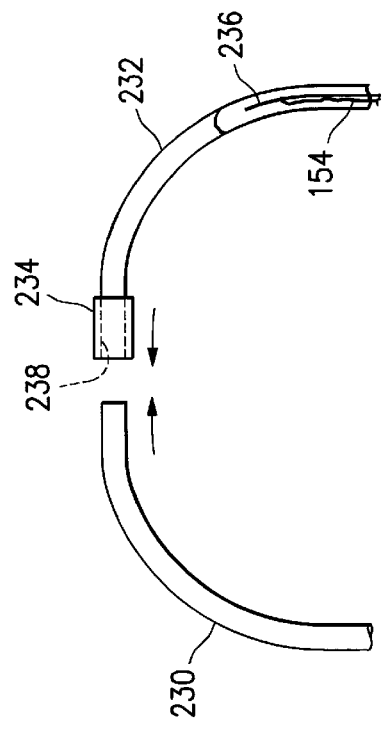
Figure 18:
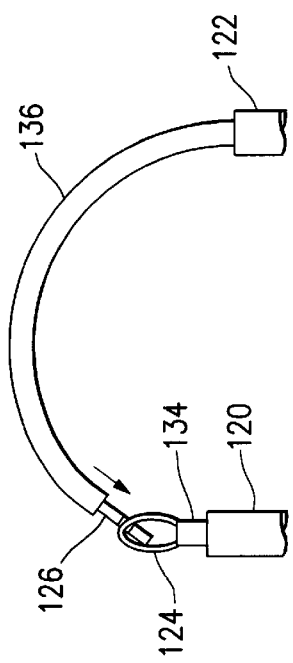

FIGS. 17–19 illustrate further embodiments in accordance with the present invention. In the embodiment illustrated in FIG. 17, both a loop advancing element 220 and a snare advancing element 222 are formed of a superelastic, SMA, or stainless steel material, and curve to meet each other. In the embodiment illustrated in FIG. 18, snare advancing element 136 is formed of a superelastic, SMA, or stainless steel material, and loop advancing element 134 is advanced directly longitudinally distally to be snared by the snare 126. In the embodiment illustrated in FIG. 19, a first curved tube 230 of a superelastic, SMA, or stainless steel material, and a second curved tube 232 of a superelastic, SMA, or stainless steel material, meet in a manner similar to the embodiment illustrated in FIG. 17. The distal ends of tubes 230, 232 mate in a somewhat different fashion, one of the tubes 230, 232 bearing a snare which is a receptacle 234 having a bore 238 having an internal diameter larger than the external diameter of the other of tubes 230, 232. Thus, when the tubes 230, 232 meet, the distal ends engage. A pushrod or wire 236, to which suture 154 is attached, is positioned in one of the lumens of tubes 230, 232, and is pushed distally down that tube, through receptacle 234, and proximally up the other of tubes 230, 232. Thus, a suture can be advanced around a blood vessel of interest in a manner similar to the embodiments described above.

FIGS. 20–24 illustrate several steps of an exemplary method in accordance with the present invention. While FIGS. 20–24 illustrate, and the following description makes reference to, ligation device 100, methods in accordance with the present invention are not limited to use of ligation device 100, and other apparatus can be utilized in practicing the present methods without departing from the spirit and scope of the present invention.

FIG. 20 illustrates the distal end of ligation device 100 after having been positioned proximate a vessel of interest in a patient, e.g., a uterine artery 10. Distal end 150 of cannula 104 is initially positioned away from vessel 10. Distal end 150 is accurately positioned within $X_{max}$ of the vessel by pointing cannula 104 in several directions around where the practitioner believes the vessel is located, monitoring the output of unit 156 for distance and velocity data to determine the relative location of the vessel relative to distal end 150, and repositioning the distal end until the distal end is a distance X from vessel 10 less than $X_{max}$. As described above, reflected ultrasound waves 182, which are preferably collimated, are received by Doppler wand 140 (or the functional components thereof, integrated into ligation device 100) and are processed by unit 156 to indicate the relative location of vessel 10. For example, Doppler sound is utilized to find the vessel location, and thereafter pulsed wave Doppler is utilized to identify a more precise location and the distance to the artery 10.

Once the practitioner has established that vessel 10 is directly distal of the distal end 150 of cannula 104, first and second actuation rings 112, 114 are moved distally to move first and second extendable members 120, 122 distally, as illustrated in FIG. 21. In yet another embodiment of the present invention, the first and second extendable members 120, 122 invaginate the tissue of the vaginal wall, and the underlying tissue beds, adjacent to vessel 10 by non-penetration such that the vessel is bracketed on two sides by invaginated tissue and members 120, 122. Then, as illustrated in FIGS. 22 and 23, suture/loop advancing element 134 and snaring element 136 are both distally advanced by pushing tabs 116, 118 distally; the advancement of elements 134 and 136 can be serial, simultaneous, or combinations thereof. Because suture/loop advancing element 134 is inside a (preferably mammalian) patient while it is advanced, the suture/loop advancing element is heated up in situ above its SMA transition temperature, and transforms from its straight configuration to its 'remembered' or curved configuration. Thus, advancement of advancing element 134 out of member 120 is accompanied by element 134 assuming, or having already assumed, its curved configuration. Element 134 and loop 124 are therefore advanced in a lateral direction and toward element 136 and snare 126.

While the loop 124 is positioned directly distal of snare 126, snaring element 136 is moved distally to advance snare 126 distally. Snare 126, and more particularly head 160, enters loop 124, and is pushed through the loop. Snare 126 is then retracted proximally so that hook portion 164 deflects loop 124 into slot 162, thus causing the loop to be grabbed by the snare. In this respect, a widened mouth to slot 162, as suggested by phantom line 168, can facilitate capture of loop 124.

With loop 124 ensnared by snare 126, snaring element 136 is retracted proximally, which pulls on the loop in a proximal direction. As the materials out of which portions 172, 174 are formed are relatively rigid (superelastic, SMA, and stainless steel being preferable), the force applied by snaring element 136 to loop 124 will cause the joint between loop 124 and slot 178 to break or otherwise release the loop from element 134. As will be readily appreciated by one of ordinary skill in the art, the joint between loop 124 and slot 178 is designed as a breakaway element, with the minimum force needed to break the joint selected so that the loop will not prematurely break free of curved portion 172, yet not so high that a practitioner will not readily be able to generate the required force by pulling proximally on tab 118. Once loop 124 has been broken free of slot 178, snaring element 136 and second extendable element 122 are further pulled proximally so that the loop is pulled into cannula 104. As described above, suture material 154 extends through curved portion 172 and is secured to loop 124, and is therefore pulled along with the loop.

Thus, suture material 154 is advanced distally past vessel 10 by distal extension of first extendable element 120 and suture/loop advancing element 134, is advanced laterally behind the vessel by curved portion 172 having assumed its curved superelastic configuration, and is advanced proximally by proximal retraction of loop 124 after having been grabbed by snare 126. Alternatively, the suture material 154 is advanced distally past vessel 10 by non-penetrating, distal invagination of tissue by the first extendable element 120, and suture/loop advancing element 134 is advanced to penetrate laterally behind the vessel by curved portion 172 having assumed its curved superelastic configuration, and is thereafter advanced proximally by proximal retraction of loop 124 after having been grabbed by snare 126. With the loop of suture material passing around vessel 10, ligation device 100 can be pulled proximally, leaving the loop of suture material around vessel 10, as illustrated in FIG. 24. At this point, the practitioner can make whatever form of ligation she chooses, as the loop of suture material has been accurately passed around the vessel 10 of interest.

FIG. 25 illustrates yet another embodiment in accordance with the present invention. The embodiment illustrated in FIG. 25 is similar to that illustrated in FIG. 3, but differs in the cross-sectional profile of the device 250. Instead of the oval cross-sectional profile illustrated in FIG. 3, device 250 includes the coplanar lumenae 130, 132, 138 defined in three adjacent and joined tubes 252, 254, 256.

FIGS. 26A and 26B illustrate alternative embodiments useful for passing and ensnaring suture material, such as suture material 154, as devices 260, 280. The device 260 includes a detachable arrowhead shaped element 262 at the end of suture/loop advancing element 134 to which a length of ligation material is attached as discussed elsewhere herein. A inwardly laterally directed opening 264 is formed in the end of snaring element 136. The opening 264 has an inner dimension selected so that the arrowhead element 262 will pass into the passageway 264 when properly aligned therewith. Once the arrowhead element 262 has passed into the opening 264, the snaring element 136 can be retracted in a manner similar to that described above, causing the arrowhead element 262 to be caught and ensnared in the interior of the snaring element, and thereafter detached from the element 134. The snaring element 136 can optionally further be provided with a second opening 266 (indicated in phantom) opposite the first opening 264, so that the arrowhead element 262 can be passed entirely through the snaring element to be ensnared.

Further optionally, the element 134 can be electrically insulated on its exterior surface proximal of the detachable arrowhead 262, as indicated by dithering 268, and element 136 can similarly be electrically insulated on its exterior surface proximal of a preselected point 270, as indicated by dithering 272. When provided with this electrical insulation, the arrowhead 262 and the portion 274 of the element 136 distal of the point 270 can be electrically connected to opposite poles of a bipolar RF electrical energy source (not illustrated) and the arrowhead can be used as an RF cutter to easily push through tissue beds and tissue planes which lie between it and the opening 264. For example, proximal portions of the elements 134, 136 can be electrically connected to an RF energy source to permit the arrowhead 262 to act as an RF cutter, as will be readily appreciated by one of ordinary skill in the art.

FIG. 26B illustrates aspects of yet another alternative embodiment in accordance with the present invention, device 280. Device 280 is similar in some respects to device 260. Device 280 includes a detachable ball 282 mounted at the distal end of element 134. The ball 282, when advanced into opening 284 or through to opening 286, is ensnared by the snaring element 136 in a manner similar to that described elsewhere herein.

Figure 27:
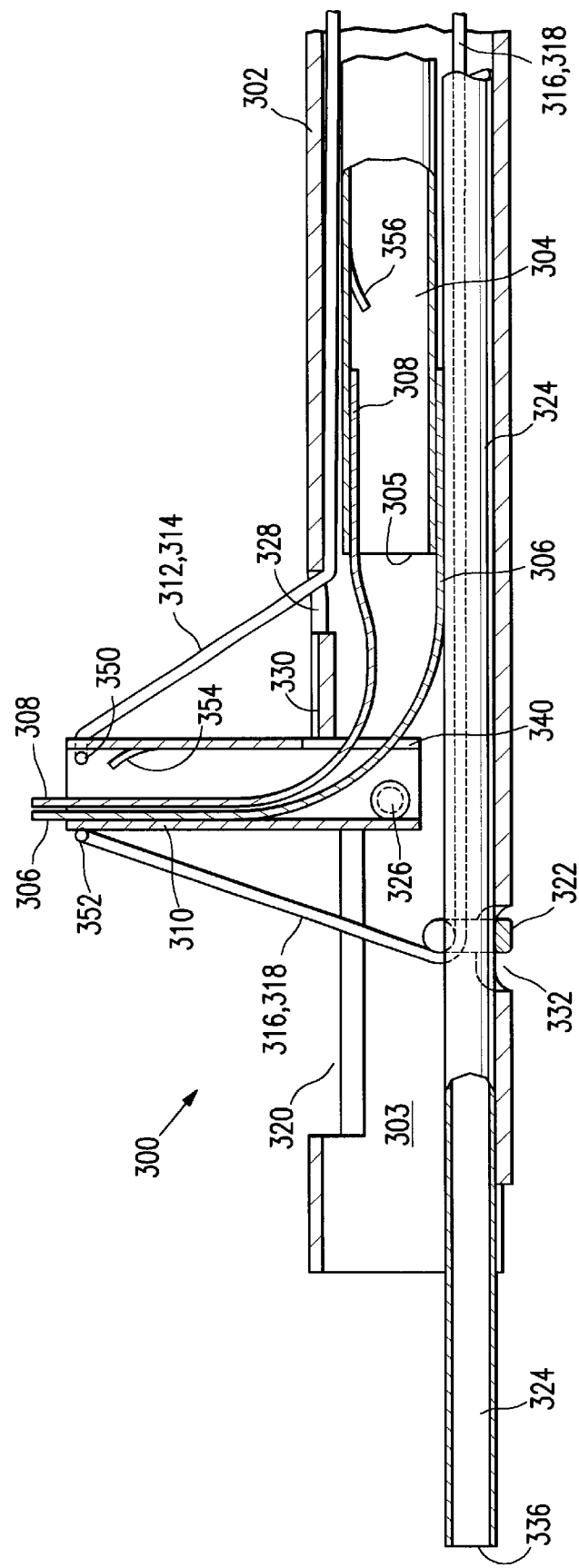
FIGS. 27–30 illustrate several views of yet another embodiment in accordance with the present invention.

FIGS. 27–30 illustrate several views of yet another embodiment in accordance with the present invention. Turning to FIG. 27, an extendible element 300 is illustrated with portions removed to aid in a better understanding of the extendible element. Element 300 can be used instead of any of the above-described extendible elements, e.g., elements 120, 122.

Element 300 includes a longitudinally extending cannula or tube 302 having a hollow interior 303. A stationary guide tube 304 is mounted in the cannula 302 and has a distal end 305 which is positioned proximally of the distal end of the tube 302. The guide tube 304 is provided to guide a pushrod or the like carrying a length of suture material (not illustrated) toward the distal end of the tube 302. A pair of wire guides 306, 308 are mounted to the top and bottom of the of the guide tube 304 adjacent to its distal end, and extend distally out of the distal end 305 of the guide tube. The guides 306, 308 are preferably formed of a flexible material and are flat in cross-section so that when a suture-bearing pushrod or the like is advanced out the distal end of the guide tube 304, the pushrod is caused to follow a path between the wire guides 306, 308.

The distal ends of the wire guides 306, 308 are positioned in a hollow arm 310, and are preferably not secured to the hollow arm. The arm 310 is attached to the cannula 302 at a pivot 326. The cannula 302 includes a window, cutout, or fenestration 320 adjacent to the arm 310, and is sized and positioned so that the arm 310 can rotate between a deployed orientation, illustrated in FIGS. 27 and 28, and a retracted orientation, illustrated in FIG. 29, without hitting or otherwise interfering with the cannula. The arm 310 can have any of a number of cross-sectional configurations, including the somewhat rectilinear shape illustrated in the embodiment of FIGS. 27–30.

The element 300 also includes two pulling elements with which the orientation of the arm 310 can be controlled. In the embodiment illustrated in FIGS. 27–30, the pulling elements include a pair of upper pullwires 312, 314, which extend from within proximal portions of the cannula 302 to an attachment region 350 on the arm 310. The pulling elements also include a pair of lower pullwires 316, 318, which extend from within proximal portions of the cannula 302 to an attachment region 352 on the arm 310. As the attachment regions 350, 352 are on opposite sides of the arm 310 (top, bottom, respectively), pulling on the pullwire pairs will result in moving the arm to either the deployed orientation or the retracted orientation. More specifically, pulling on the upper pullwire pair 312, 314 causes the arm to rotate clockwise (in the view illustrated in FIG. 27), So that the arm extends generally transverse to the cannula 302. Conversely, pulling on the lower pullwire pair 316, 318 causes the arm to rotate counterclockwise (again, in the view illustrated in FIG. 27), so that the arm is within the cannula's hollow interior and extends longitudinally.

Figure 29:
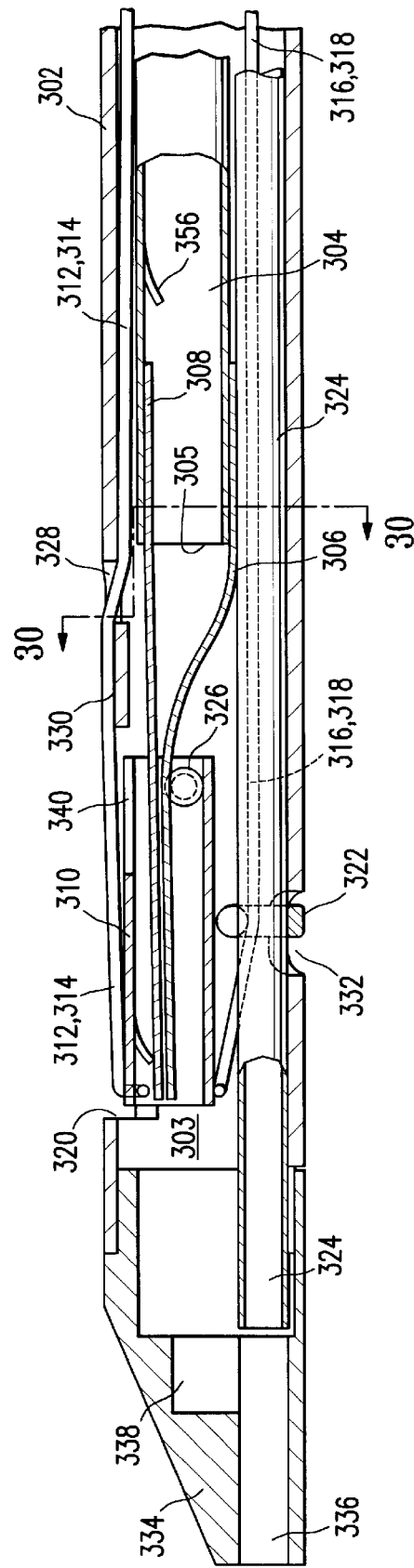
Figure 30:
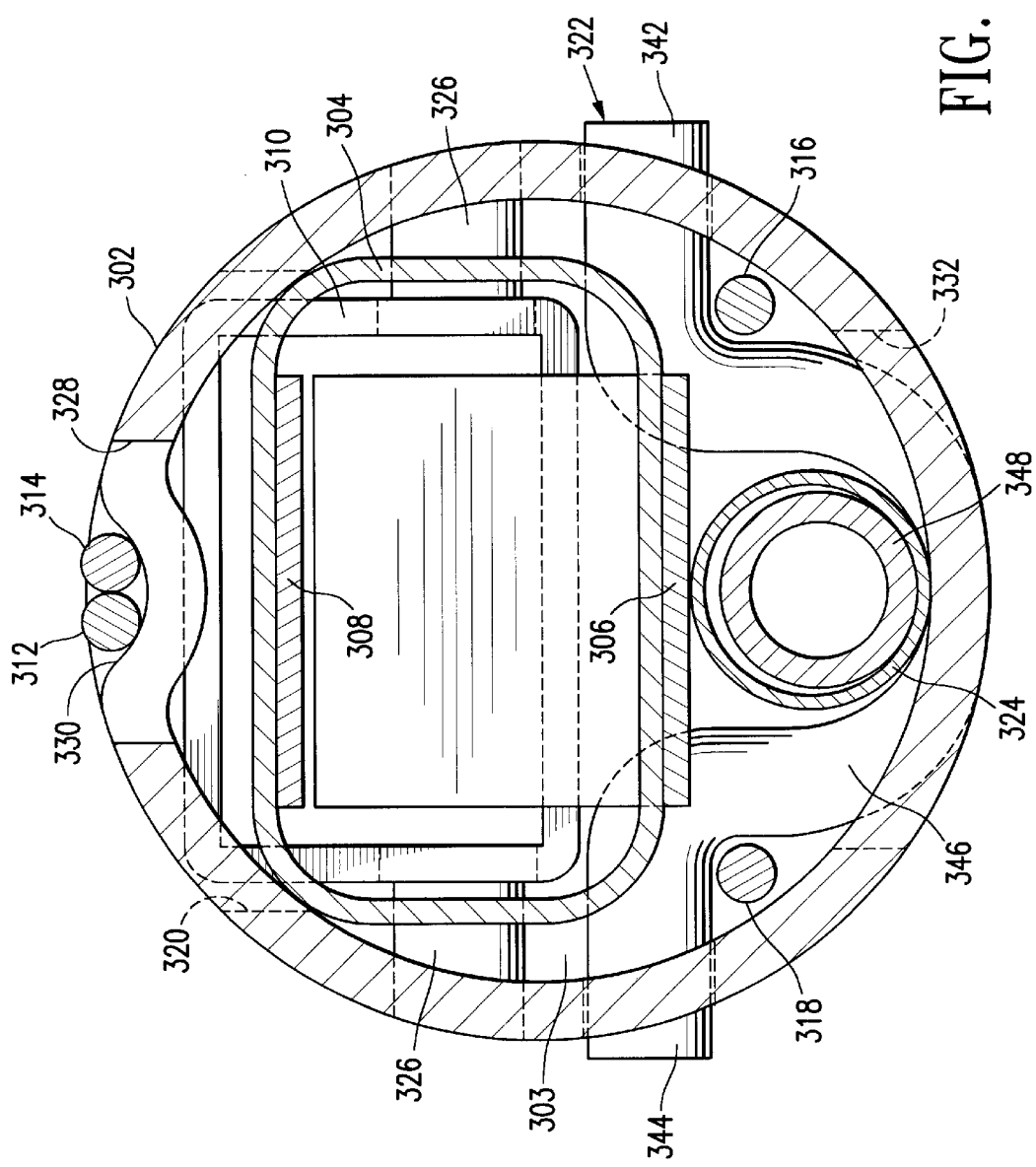

The element 300 preferably includes one or more structures which facilitates operation of the upper pullwires 312, 314. A port 328 is preferably formed through the cannula wall somewhat proximally of the fenestration 320, and the upper pullwire pair extends through this upper port. Additionally, a groove or trough 330 is optionally formed in the outer surface of the cannula between the port 328 and the fenestration 320. The trough 330 is sized to be deep enough to receive the upper pullwire pair so that when the arm 310 is in the retracted orientation, the pullwires are positioned in the trough and do not extend much or at all beyond the outer diameter of the cannula. FIGS. 29 and 30 illustrate the arm 310 in the retracted orientation, and the upper pullwires 312, 314 positioned in the trough 330. Thus, the proximal lip of the port 328 acts as a bearing surface for the upper pullwires 312, 314 as they move longitudinally and the arm 310 pivots about pivot 326.

Figure 28:
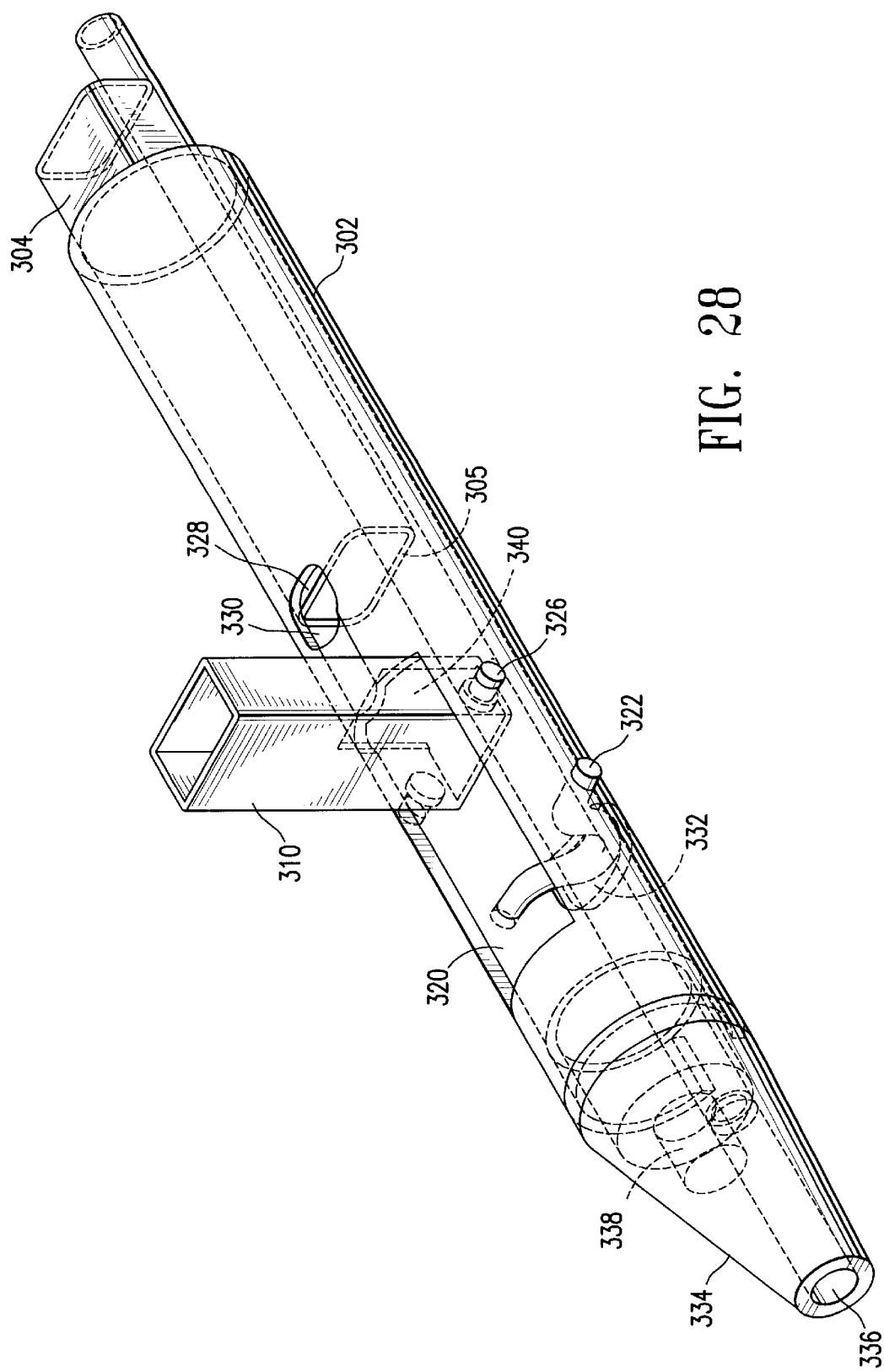

The element 300 preferably includes structure which permits the lower pullwires to rotate the arm 310. In the embodiment illustrated in FIGS. 27–30, a yolk 322 is positioned in the cannula 302 with the lower pullwires 316, 318 extending around the yolk. FIGS. 28 and 30 better illustrate details of the yolk 322. The yolk 322 is mounted in the cannula 302 distally of the pivot point 326 and preferably below the pivot point. As will be readily appreciated from FIGS. 27–30, pulling proximally on pullwires 316, 318 results in the arm 310 rotating down into the cannula 302 through the fenestration 320, and into the retracted orientation. For ease of positioning the yolk 322 into the element 300, the cannula 302 may optionally include an opening 332 into which the yolk partially extends. The opening 332 can be eliminated.

Also illustrated in FIG. 27 is a stationary tube 324 which extends along the bottom of the cannula 302. The stationary tube 324 is provided so that a practitioner can advance other tools through the element 300 without interfering with the operation of the arm 310. By way of example and not of limitation, tools such as an anesthesia needle or the like can be advanced distally through the tube 324 from its proximal end (not illustrated) to its distal end 336 (see FIG. 28). The arm 310 also preferably includes a cutout portion 340 on the upper surface of the arm (when in the retracted position; on the proximal face when in the deployed orientation) through which the wire guides 306, 308 extend. The cutout 340 is provided so that a pushrod carrying a suture (not illustrated) can follow a path into the arm 310 which is more gently curved than if the cutout is not provided, and therefore the cutout facilitates use of the element 300 to pass a length of suture material around a blood vessel. Fingers 354, 356 are also optionally provided adjacent to structures in the element 300 on which a suture may snag during deployment, such as attachment portion 350 and the proximal end of the wire guides 306, 308. The fingers 354, 356 provide a ramp to deflect the advancing suture away from the structure against which the suture may snag, and therefore facilitate use of the element 300.

Turning now to FIG. 28, the element 300 preferably includes a distalmost tapered tip 334 in which the distal port 336 of the tube 324 is formed. The tip 334 optionally includes a blind bore 338 in its interior which facilitates assembly of the tip to the cannula 302. Also illustrated in FIG. 28 is the yolk 322 secured to the interior of the cannula 302 with the stationary tube 324 extending over the yolk and for which the yolk is provided with a unique shape.

FIG. 29 illustrated the element 300 with the arm 310 in its retracted orientation resulting from the lower pullwires 316, 318 having been pulled proximally. As illustrated in FIG. 29, the free distal ends of the wire guides 306, 308 are, when the arm 310 is in the retracted orientation, preferably within the hollow interior of the arm, so that the wire guides do not interfere with the arm passing through the fenestration 320 and into the interior of the cannula 302.

FIG. 30 illustrates a cross-sectional view of the element 300, taken at line 30–30 in FIG. 29. Beginning at the top of the figure, the upper pullwires 312, 314 are illustrated in the trough 330. The exemplary cross-sectional shape of the arm 310 (rectilinear) can be seen as well as the generally rectilinear cross-sectional shape of the guide tube 304. The yolk 322 includes a pair of arms 342, 344, which are secured to the interior of the cannula 302. A U-shaped curved middle portion 346 extends between the two yolk arms 342, 344, and is sized to receive the tube 324 therethrough. The lower pullwires 316, 318 extend around the yolk arms 342, 344, and the yolk acts as a bearing surface for the pullwires to pull the arm 310 back into the cannula 302. Also illustrated in FIG. 30 is an exemplary tool 348 extending through the tube 324, e.g., an anesthesia needle. Optional opening 332 is also illustrated.

The operation of the embodiment illustrated in FIGS. 27–30 will now be described with reference to the drawing figures. The element 300 is extended adjacent to a blood vessel of interest, as described above with reference to FIGS. 1–26. According to an alternate embodiment of the present invention, element 300 is invaginally extended adjacent to a blood vessel of interest by non-penetration, as further described herein. Optionally, anesthesia can be administered using a needle, e.g., needle 348. Once in position, the upper pullwires 312, 314 are pulled proximally, which rotates the arm 310 out of the cannula 302 and into the deployed orientation. Thereafter, a pushrod or the like, carrying a length of suture material 154, is advanced distally through the tube 304, between the wire guides 306, 308, laterally into the interior of the arm 310 and still between the wire guides 306, 308, and out of the arm 310. The suture is then snared by a snaring element such as those previously described, and pulled proximally, thus looping the length of suture material around the blood vessel of interest. The lower pullwires 316, 318 can be pulled proximally to rotate the arm 310 back into the cannula 302 when desired.

FIGS. 31–34 illustrate several steps of yet another exemplary method in accordance with the present invention. While FIGS. 31–34 illustrate, and the following description makes reference to, ligation device 100 and ligation device 300, methods in accordance with the present invention are not limited to use of such devices, and other apparatus can be utilized in practicing the present methods without departing from the spirit and scope of the present invention.

Figure 31:
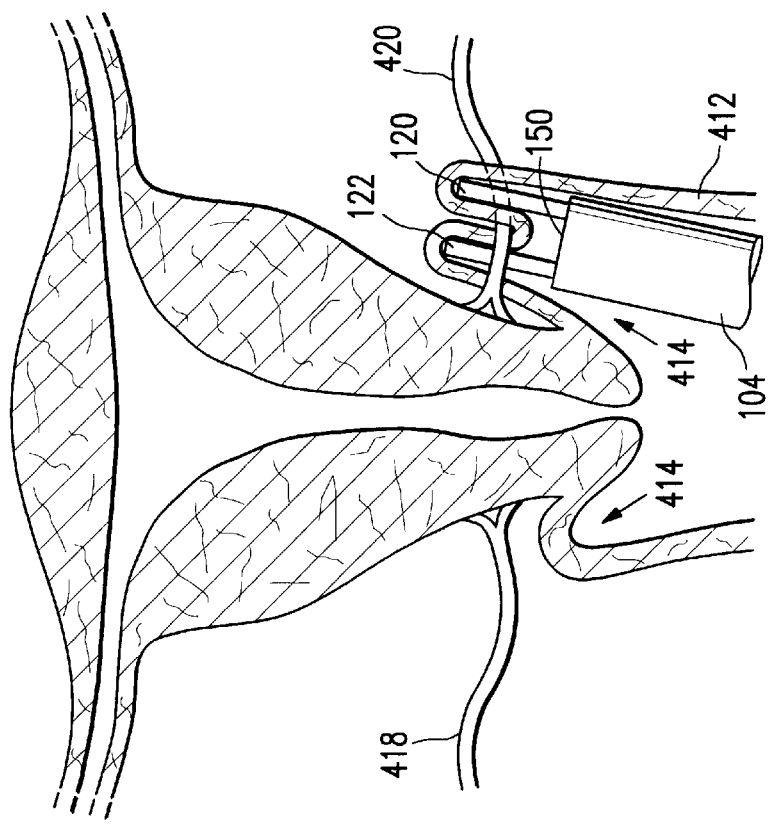
FIG. 31 illustrates the device of FIG. 1 used in accordance with an exemplary embodiment of a method of ligating a uterine artery in accordance with the present invention.

FIG. 31 illustrates the device of FIG. 1 used in accordance with an exemplary embodiment of a method of ligating a uterine artery in accordance with the present invention. The distal end of a ligation device 100 after having been positioned proximate a vessel of interest in a patient, e.g., a uterine artery 420 is used to invaginate the vaginal fornix 414. First, the distal end 150 of cannula 104 is inserted through the vagina 412 until it approaches the artery 420, e.g., up to the vaginal fornix 414. Then, first extendable member 120 and second extendable member 122 are advanced distally and generally toward the artery 420 to invaginate the vaginal wall and the tissue adjacent to the vaginal wall. The artery 420 is enclosed by the invaginated tissue on at least two sides without penetrating the tissue. By way of example and not by limitation, the artery 420 may be identified and/or located within a tissue bundle via a Doppler wand located in cannula 104, as previously described.

Figure 32:
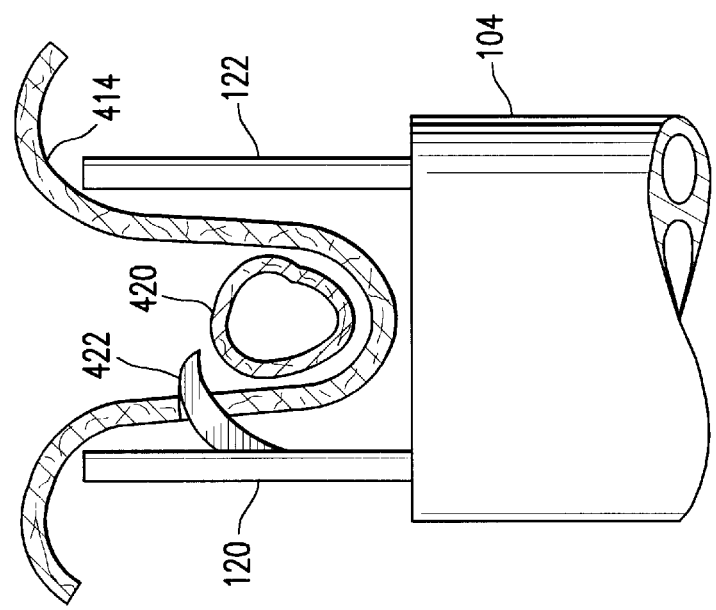
FIG. 32 illustrates the device of FIG. 1 used in accordance with an exemplary embodiment of a method of ligating an anatomical feature in a patient by invagination.

FIG. 32 illustrates the device of FIG. 1 used in accordance with an exemplary embodiment of a method of ligating an anatomical feature in a patient by invagination. An aspect of the present invention includes a first extendable element 120 having a tissue penetrating member 422. Once the first and second extendable elements 120, 122 are in position and have invaginated the vaginal fornix 414 around artery 420, tissue penetrating member 422 is activated to penetrate the tissue bundle and ligate the artery 420. Artery 420 may be ligated by any of the embodiments previously described. Tissue penetrating member 422 is thereafter withdrawn leaving the artery 420 ligated. The procedure may then be repeated to ligate the other artery 418.

Figure 33:
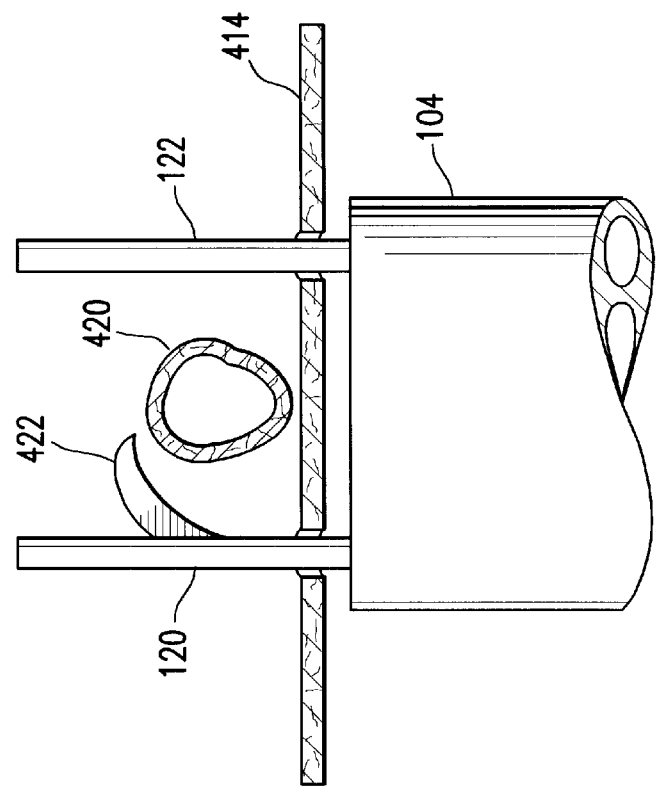
FIG. 33 illustrates the device of FIG. 1 used in accordance with an exemplary embodiment of a method of ligating an anatomical feature in a patient by penetration.

FIG. 33 illustrates the device of FIG. 1 used in accordance with an exemplary embodiment of a method of ligating an anatomical feature in a patient via penetration. An aspect of the present invention includes a first extendable element 120 having a tissue penetrating member 422. Once the first and second extendable elements 120, 122 are in position and have penetrated the vaginal fornix 414 around artery 420, tissue penetrating member 422 is activated to penetrate the tissue bundle and ligate the artery 420. Artery 420 may be ligated by any of the embodiments previously described. Tissue penetrating member 422 is thereafter withdrawn leaving the artery 420 ligated. The procedure may then be repeated to ligate the other artery 418.

Figure 34:
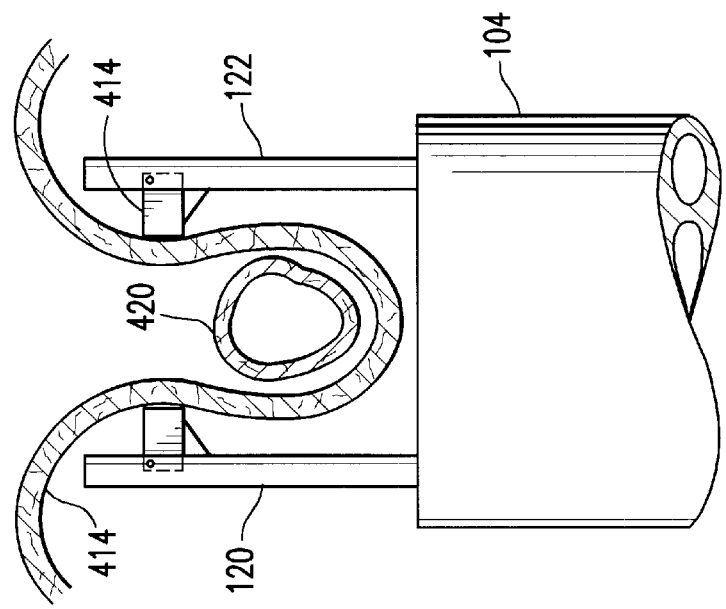
FIG. 34 illustrates the device of FIG. 27 used in accordance with an exemplary embodiment of a method of ligating an anatomical feature in a patient by invagination.

FIG. 34 illustrates the device of FIG. 27 used in accordance with an exemplary embodiment of a method of ligating an anatomical feature in a patient by invagination. The distal end of a ligation device 300 after having been positioned proximate a vessel of interest in a patient, e.g., a uterine artery 420 is used to invaginate the vaginal fornix 414. First, the distal end of cannula 302 is inserted through the vagina 412 until it approaches the artery 420, e.g., up to the vaginal fornix 414. Then, arm 310 is advanced towards the artery 420 to invaginate the vaginal wall and the tissue adjacent to the vaginal wall without penetration. The artery 420 is enclosed by the invaginated tissue on at least two sides without penetrating the tissue. By way of example and not by limitation, the artery 420 may be identified and/or located within a tissue bundle via a Doppler wand located in cannula 302, as previously described.

While the invention has been described in detail with reference to preferred embodiments thereof, it will be apparent to one skilled in the art that various changes can be made, and equivalents employed, without departing from the scope of the invention.

What is claimed is:

1. A method of preparing an anatomical vessel contained within a tissue bundle for ligation, comprising the steps of:

positioning a cannula adjacent to said tissue bundle, wherein said positioning is non-penetrating, said cannula including a first extendable member, a second extendable member, a Doppler wand, and a distal end;

transmitting ultrasound signals toward said vessel through said tissue bundle with said Doppler wand;

receiving ultrasound signals reflected by said vessel through said tissue bundle with said Doppler wand;

invaginating said tissue bundle with said first extendable member on a first side of said tissue bundle;

invaginating said tissue bundle with said second extendable member on a second side of said bundle opposite said first side; and interpenetrating a length of ligation material between said first and second extendable members on a side of said vessel opposite said cannula distal end.

2. The method as set forth in claim 1, wherein said first extendable member includes a detachable element to which said ligation material is attached, and further comprising grabbing said detachable element with portions of said second extendable member.

3. The method as set forth in claim 1, further comprising the steps of:

retracting said second extendable member in a proximal direction; and releasing said detachable element from said first extendable member.

4. The method as set forth in claim 1, wherein said first extendable member includes a tissue penetrating element to which said ligation material is attached, and further comprising piercing said tissue penetrating element into said tissue bundle.

5. The method as set forth in claim 4, wherein said tissue penetrating element includes a detachable element to which said ligation material is attached, and further comprising grabbing said detachable element with portions of said second extendable member.

6. The method as set forth in claim 4, further comprising the steps of:

retracting said second extendable member in a proximal direction; and releasing said detachable element from said first extendable member.

7. A ligation device for occluding a blood vessel contained within a tissue bundle, comprising:

a cannula having a distal end that is configured for positioning adjacent the tissue bundle;

an ultrasound signals transmitter and an ultrasonic receiver configured to detect the blood vessel within tissue bundle;

a first elongated member configured to invaginate the tissue on a first side of the tissue bundle;

a second elongated member configured to invaginate the tissue on a second side of bundle opposite the first side; and a penetrating member configured for advancing a length of ligation material between the first and second elongated members on a side of the blood vessel opposite the cannula distal end.

8. The device as set forth in claim 7, wherein the first elongated member comprises a first extendable member having a detachable element attached to the ligation material, and further comprising a snare member configured for grabbing the detachable element.

9. The device as set forth in claim 8, wherein second elongated member includes a second extendable member, wherein the second extendable member is further configured to be retracted in a proximal direction, and further comprising a release mechanism configured for releasing the detachable element from the first extendable member.

10. The device as set forth in claim 8, wherein first extendable member includes a tissue penetrating element attached to the ligation material, and further comprising a piercing element configured for piercing the tissue penetrating element into the tissue bundle.

11. The device as set forth in claim 10, wherein the tissue penetrating element includes a detachable element attached to the ligation material, and further comprising a capture element configured for grabbing the detachable element.

12. The device as set forth in claim 10, wherein the second elongated member is further configured to be retracted in a proximal direction, and further comprising a release configured for releasing the detachable element from the first extendable member.

13. A ligation device for occluding a blood vessel contained within a tissue bundle, comprising:

a cannula having a distal end that is configured for positioning adjacent the tissue bundle;

an ultrasound means to detect the blood vessel within the tissue bundle;

a first elongated means to invaginate tissue on a first side of the tissue bundle;

a second elongated means to invaginate tissue on a second side of the tissue bundle opposite the first side; and a penetrating means for advancing a length of ligation material between the first and second elongated means on a side of the blood vessel opposite the cannula distal end.

* * * * *